US006341599B1

(12) United States Patent
Hada et al.

(10) Patent No.: US 6,341,599 B1
(45) Date of Patent: Jan. 29, 2002

(54) POWER SUPPLY CONTROL SYSTEM FOR HEATER USED IN GAS CONCENTRATION SENSOR

(75) Inventors: Satoshi Hada, Kariya; Kazuhiro Okazaki, Aichi-ken; Yukihiro Yamashita, Kariya; Satoshi Haseda, Okazaki, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/417,303

(22) Filed: Oct. 13, 1999

(30) Foreign Application Priority Data

Oct. 13, 1998 (JP) .......................... 10-290208
Jul. 8, 1999 (JP) .......................... 11-194822

(51) Int. Cl.[7] .............................................. F02B 75/08
(52) U.S. Cl. ...................................... 123/688; 123/697
(58) Field of Search ............................. 123/688, 697, 123/677

(56) References Cited

U.S. PATENT DOCUMENTS

| 5,340,462 | A | * | 8/1994 | Suzuki | 123/697 |
| 5,671,721 | A | * | 9/1997 | Aoki | 123/688 |
| 5,719,778 | A | | 2/1998 | Suzumura et al. | 364/477.01 |
| 5,852,228 | A | * | 12/1998 | Yamashita et al. | 123/697 |
| 6,094,975 | A | * | 8/2000 | Hasegawa et al. | 123/688 |
| 6,136,169 | A | * | 10/2000 | Okamoto | 123/688 |

FOREIGN PATENT DOCUMENTS

| GB | 2 310 725 | 9/1997 |
| JP | 61-132851 | 6/1986 |
| JP | 63-249046 | 10/1988 |
| JP | 8-278279 | 10/1996 |
| JP | 9-292364 | 11/1997 |
| JP | 10-260152 | 9/1998 |

\* cited by examiner

*Primary Examiner*—John Kwon
(74) *Attorney, Agent, or Firm*—Pillsbury Winthrop LLP

(57) ABSTRACT

A heater control system is provided for controlling the temperature of a heater used to heat a solid electrolyte-made sensing element of a gas concentration sensor up to a given temperature at which the sensing element is activated to provide a desired gas concentration output for controlling a preselected variable used in a given feedback control system. The heater control system controls an electric power supplied to the heater to bring the temperature of the sensing element into agreement with a target temperature value and determines the target temperature value as a function of the preselected variable used in the feedback control system so that only desired quantity of power may be supplied to the heater, thereby minimizing a consumption of the power.

24 Claims, 16 Drawing Sheets

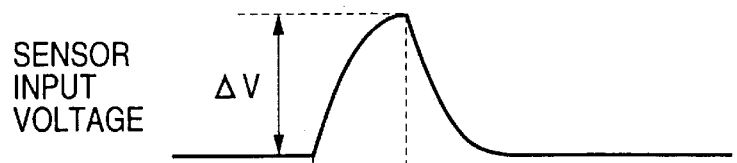
FIG. 8(a) SENSOR INPUT VOLTAGE ΔV
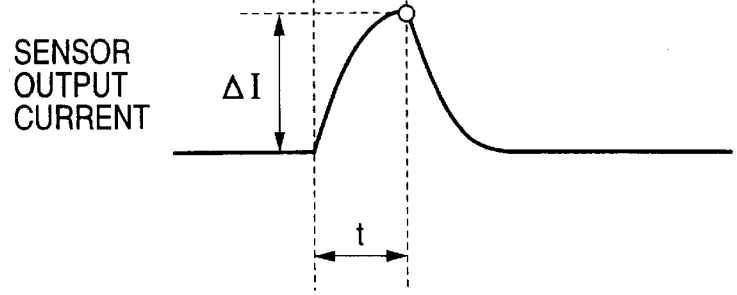
FIG. 8(b) SENSOR OUTPUT CURRENT ΔI
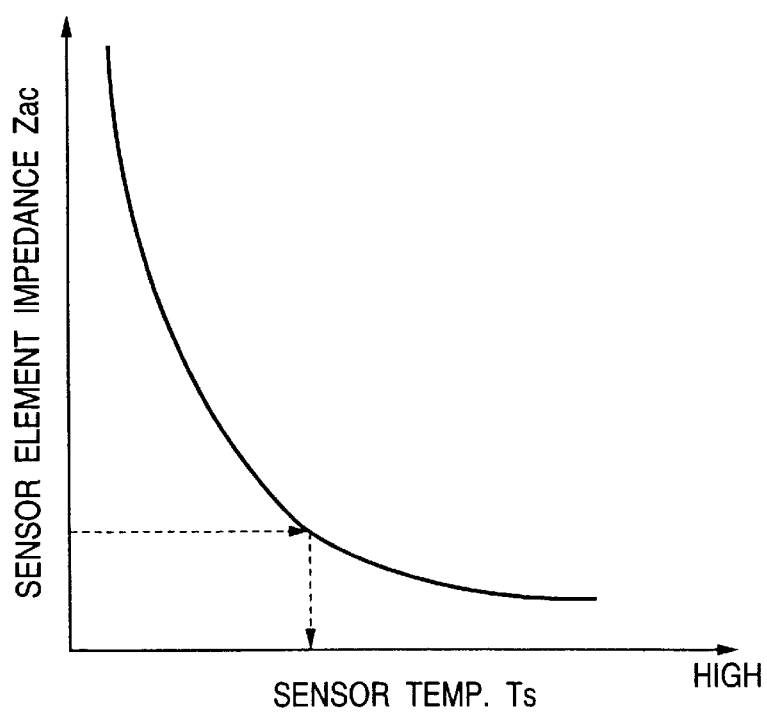
FIG. 9

POWER SUPPLY CONTROL SYSTEM FOR HEATER USED IN GAS CONCENTRATION SENSOR

BACKGROUND OF THE INVENTION

1. Technical Field of the Invention

The present invention relates generally to a heater control system for a gas concentration sensor which may be employed in an air-fuel ratio control system for automotive vehicles for measuring the concentration of gas such as $O_2$, NOx, or CO.

2. Background Art

Japanese Patent First Publication No. 61-132851 teaches one of conventional power supply systems for limiting current oxygen sensors used to measure an oxygen content in exhaust gasses of an internal combustion engine. The power supply system is designed based on the fact that an internal resistance of the limiting current oxygen sensor and a resistance value of an installed heater are usually changed with a change in surrounding temperature and determines the electric power required for activation of the oxygen sensor based on operating conditions of the engine to correct the electric power supplied to the heater as a function of the internal resistance of the oxygen sensor and the resistance value of the heater.

Japanese Patent First Publication No. 63-249046 teaches a power supply system which supplies a full power to a heater of an oxygen sensor until an internal resistance of the oxygen sensor and a resistance value of the heater each reach the value corresponding to a selected temperature and controls the power supply to the heater so as to keep the internal resistance of the heater constant.

Further, Japanese Patent First Publication No. 8-278279 teaches another type of power supply system which supplies a full power to a heater of an oxygen sensor until the temperature of the heater reaches a given initial heating temperature and controls the power supply to the heater as a function of the temperature of a sensor element after reaching a selected value.

The above described power supply systems are all designed to control the power supply to the heater so as to keep the sensing element at a given activating temperature (about 700°) regardless of operating conditions of the internal combustion engine or other preselected conditions. Specifically, a large amount of power is consumed in operating the gas sensor, which does not meet the energy saving required in automobile technologies in recent years.

For instance, the consumption of electric power in automotive vehicles usually results in an increase in fuel economy. It is, thus, known that the reduction in energy consumption in electric parts is important to increase the fuel economy of the automotive vehicles. Particularly, in the case of hybrid cars using an electric motor, the consumption of electric power increases the consumption of fuel more greatly than in gasoline-fueled automobiles.

SUMMARY OF THE INVENTION

It is therefore a principal object of the present invention to avoid the disadvantages of the prior art.

It is another object of the present invention to provide a heater control system for gas concentration sensors which is designed to allow the sensor to provide an accurate sensor output with an decreased power consumption.

According to one aspect of the invention, there is provided a heater control apparatus for controlling a temperature of a heater used to heat a solid electrolyte-made sensing element of a gas concentration sensor up to a temperature at which the sensing element is activated to provide a desired gas concentration output. The heater control apparatus comprises: (a) a power supply controlling circuit controlling an electric power supply to the heater to bring one of a temperature of the sensing element of the gas concentration sensor and a temperature of the heater into agreement with a target temperature value; and (b) a target temperature value determining circuit determining the target temperature value as a function of an environmental condition in which the gas concentration sensor is used and a use of the gas concentration sensor.

In the preferred mode of the invention, the target temperature value determining circuit changes the target temperature value based on whether it is required to use the gas concentration output from the gas concentration sensor or not.

The target temperature value determining circuit decreases the target temperature value when it is not required to use the gas concentration output from the gas concentration sensor and increases the target temperature value when it is required to use the gas concentration output.

The gas concentration sensor is designed to measure the concentration of a given gaseous component contained in either of exhaust gasses and induction gasses of an internal combustion engine of a vehicle and provide the gas concentration output indicative thereof for use in feedback control of an air-fuel ratio of mixture supplied to the internal combustion engine. A decision circuit is provided for deciding whether a given control execution condition is met or not which is used in determining whether the feedback control of the air-fuel ratio is to be executed or not. The target temperature value determining circuit changes the target temperature value depending upon a decision of the decision circuit.

The gas concentration sensor measures the concentration of oxygen contained in exhaust gasses or induction gasses of the engine to determine an air-fuel ratio for use in feedback control of an air-fuel ratio of mixture supplied to the engine. The target temperature value determining circuit changes the target temperature value as a function of the air-fuel ratio determined by the gas concentration sensor.

When the air-fuel ratio determined by the gas concentration sensor is leaner than a stoichiometric air-fuel ratio, the target temperature value determining circuit elevates the target temperature value above that determined when the air-fuel ratio determined by the gas concentration sensor shows the stoichiometric air-fuel ratio.

When the air-fuel ratio determined by the gas concentration sensor is richer than a stoichiometric air-fuel ratio, the target temperature value determining circuit elevates the target temperature value above that determined when the air-fuel ratio determined by the gas concentration sensor shows the stoichiometric air-fuel ratio.

When a mixture supplied to the internal combustion engine is controlled to be leaner than the stoichiometric air-fuel ratio, the target temperature value determining circuit may elevate the target temperature value above that when the mixture supplied to the internal combustion engine is controlled to have the stoichiometric air-fuel ratio.

When the mixture supplied to the internal combustion engine is controlled to be richer than a stoichiometric air-fuel ratio, the target temperature value determining circuit may elevate the target temperature value above that when the mixture supplied to the internal combustion engine is controlled to have the stoichiometric air-fuel ratio.

The gas concentration sensor is controlled by the air-fuel ratio feedback control system to selectively output an electromotive force signal according the concentration of oxygen when the air-fuel ratio of mixture lies within a narrower range across a stoichiometric air-fuel ratio and a limiting current signal changing linearly with a change in the air-fuel ratio of mixture when the air-fuel ratio changes within a wider range from a rich air-fuel ratio to a lean air-fuel ratio. The target temperature value determining circuit changes the target temperature value depending upon whether the gas concentration sensor is outputting the electromotive force signal or the limiting current signal.

The target temperature value determining circuit may alternatively change the target temperature value depending upon whether the gas concentration sensor is controlled by the air-fuel ratio feedback control system to output the electromotive force signal or the limiting current signal.

The gas concentration sensor may be designed to output a plurality of signals indicating given parameters different from each other, temperatures of the heater required to indicate the given parameters correctly being different. In this case, the target temperature value determining circuit may change the target temperature value based on the parameters indicated by the signals outputted by the gas concentration sensor.

The gas concentration sensor may be employed in a hybrid vehicle which uses both an internal combustion engine and an electric motor as a power source for driving the hybrid vehicle. In this case, the target temperature value determining circuit may decrease the target temperature value when the internal combustion engine is at rest.

A sensor deterioration determining circuit may also be provided for determining the degree of deterioration of the gas concentration sensor. The target temperature value determining circuit may correct the target temperature value so as to compensate for the degree of deterioration of the gas concentration sensor determined by the sensor deterioration determining circuit.

According to the second aspect of the invention, there is provided a heater control apparatus for controlling a temperature of a heater used to heat a solid electrolyte-made sensing element of a gas concentration sensor up to a temperature at which the sensing element is activated to provide a desired gas concentration output for controlling a preselected variable used in a given feedback control system. The heater control apparatus comprises: (a) a power supply controlling circuit controlling an electric power supply to the heater to bring one of a temperature of the sensing element of the gas concentration sensor and a temperature of the heater into agreement with a target temperature value; and (b) a target temperature value determining circuit determining the target temperature value as a function of the preselected variable used in the feedback control system.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 8(a) shows a change in voltage produced when the impedance of a sensor element is used;

FIG. 8(b) shows a change in current flowing through a sensor element which is used to determine the impedance of a sensor element;

FIG. 9 is a graph which shows a relation between the impedance of a sensor element and the temperature of the sensor element;

DESCRIPTION OF THE PREFERRED EMBODIMENTS

Figure 1:
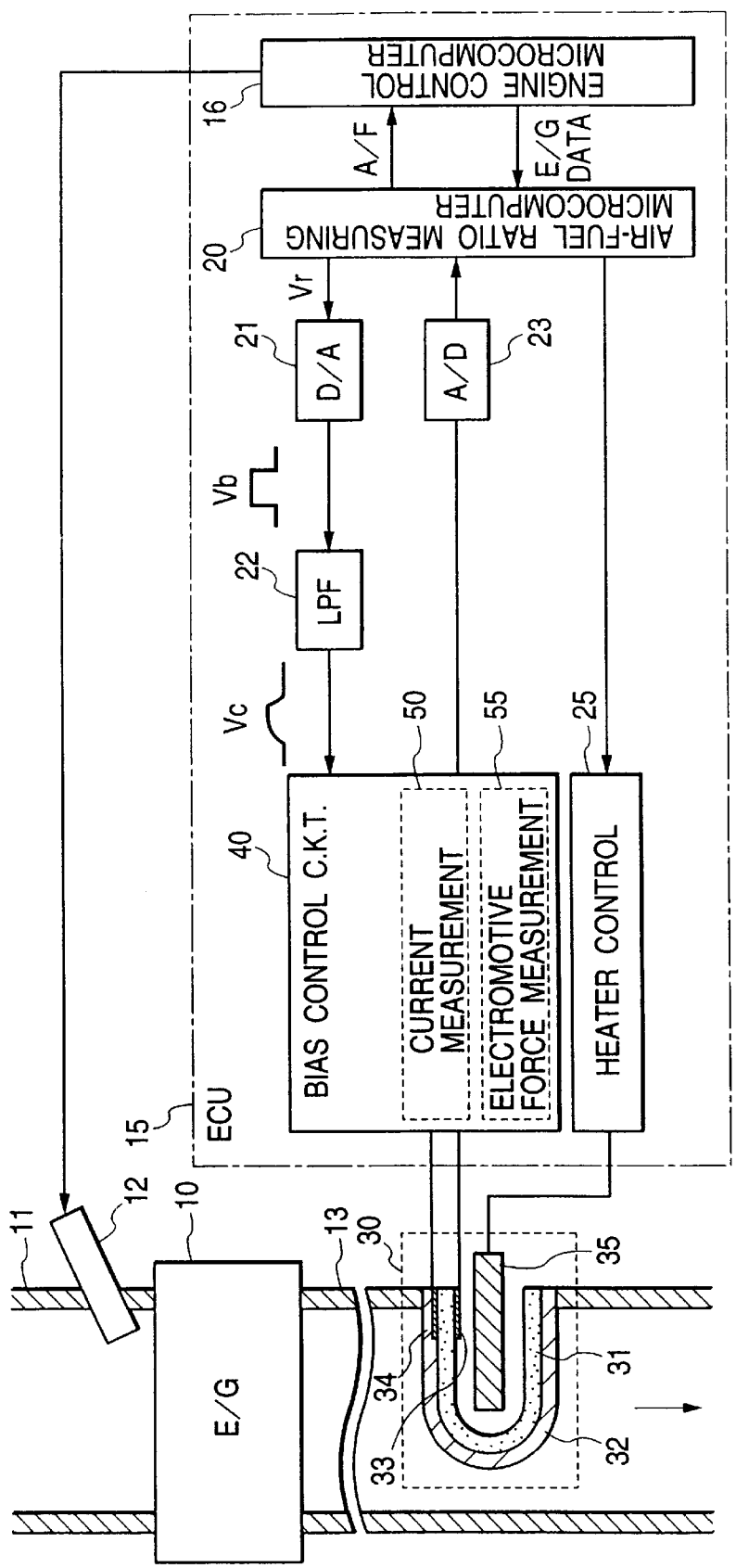
FIG. 1 is a block diagram which shows a gas sensor control system according to the invention used with an air-fuel ratio control system for automotive vehicles.

Referring now to the drawings, wherein like numbers refer to like parts in several views, particularly to FIG. 1, there is shown a gas sensor control system according to the first embodiment of the invention which is used with an air-fuel ratio control system for automotive vehicles. The air-fuel ratio control system, as discussed below, is designed to control the quantity of fuel injected into an internal combustion engine as a function of an output of an air-fuel ratio sensor installed in an exhaust pipe under feedback (F/B) control to bring the air-fuel ratio into agreement with a target value. Hereinafter, a measuring procedure for measuring the air-fuel ratio using an output of the air-fuel ratio sensor, a measuring procedure for measuring the internal resistance of the air-fuel ratio sensor, and a control procedure for controlling the power supply to a heater installed in the air-fuel ratio sensor will be described.

In FIG. 1, the engine 10 is a multi-cylinder four-cycle internal combustion engine. An injector 12 is installed in an intake pipe 11 to inject the fuel into each cylinder of the engine 10. A cup-shaped air-fuel ratio (A/F) sensor 30 is installed in an exhaust pipe 13. The A/F sensor 30 is a limiting current gas sensor designed to output an limiting current signal whose level changes linearly in proportion to the concentration of oxygen contained in exhaust gasses or carbon monoxide in unburnt gasses.

The A/F sensor 30 consists of a solid electrolyte body 31, a diffused resistance layer 32, inner and outer electrodes 33 and 34, and a heater 35. The solid electrolyte body 31 is made of an oxygen ion conductive oxide sintered body. The diffused resistance layer 32 is made of a heat resisting inorganics. The inner and outer electrodes 33 and 34 are each made of a noble metal such as platinum having a high catalytic activity and coated chemically with a porous material. The inner electrode 33 is formed on an inner surface of the solid electrolyte body 31 and exposed to the air used as a reference gas. The outer electrode 34 is formed on an outer surface of the solid electrolyte body 31 and exposed to exhaust gasses in the exhaust pipe 13.

The air-fuel ratio control system also includes an electronic control unit (ECU) 15 which consists of an engine control microcomputer 16, an air-fuel ratio measuring microcomputer 20, a D/A converter 21, a low-pass filter 22, an A/D converter 23, a heater control circuit 25, and a bias control circuit 40.

The engine control microcomputer 16 monitors engine speed, intake air pressure, coolant temperature, throttle opening, etc. through sensors (not shown) to determine engine operating conditions and controls the injector 12 to adjust the quantity of fuel injected to the engine 10 to a target value.

The air-fuel ratio measuring microcomputer 20 is connected to the engine control microcomputer 16 to receive engine control data to control the heater control circuit 25 and the bias control circuit 40 and transmit air-fuel ratio data to adjust the quantity of fuel supplied to the engine 10 through the injector 12. Specifically, the air-fuel ratio measuring microcomputer 20 measures the value of current flowing through the A/F sensor 30 when applied with the voltage to determine the air-fuel ratio as a function of the measured value of current using a map shown in FIG. 3 and outputs a signal indicative of the determined air-fuel ratio to the engine control microcomputer 16. The air-fuel ratio measuring microcomputer 20 also controls the heater control circuit 25 to adjust the amount of current supplied to the heater 35 for keeping the A/F sensor 30 activated normally.

The air-fuel ratio measuring microcomputer 20 provides a bias command signal Vr to the D/A converter 21. The D/A converter 21 converts the input into an analog signal Vb and outputs it to the low-pass filter 22. The low-pass filter 22 removes high-frequency components from the analog signal Vb to produce a voltage signal Vc which is, in turn, inputted to the bias control circuit 40. The bias control circuit 40 is responsive to the voltage signal Vc to selectively apply an air-fuel ratio measuring voltage and a sensor element resistance measuring voltage, as will be described later in detail, to the A/F sensor 30. When it is required to measure the air-fuel ratio using the A/F sensor 30, the voltage selected as a function of the measured air-fuel ratio is applied to the A/F sensor 30. Alternatively, when it is required to measure the resistance value of a sensor element (i.e., the solid electrolyte body 31) of the A/F sensor 30, the sensor element resistance measuring voltage having a given time constant is applied to the A/F sensor 30 in the form of a single shot.

The bias control circuit 40 includes a current measuring circuit 50 and an electromotive force measuring circuit 55. The A/F sensor 30, when applied with the voltage, produces a limiting current as a function of an oxygen content in exhaust gasses. The current measuring circuit 50 measures the limiting current outputted from the A/F sensor 30. The electromotive force measuring circuit 55 measures an electromotive force outputted from the A/F sensor 30 which changes in level depending upon whether the air-fuel ratio is on a rich side or a lean side of the stoichiometric air-fuel ratio. Outputs of the current measuring circuit 50 and the electromotive force measuring circuit 55 are inputted to the air-fuel ratio measuring microcomputer 20 through the A/D converter 23. The heater control circuit 25 controls a power supply to the heater 35 under duty control based on the temperature of the A/F sensor 30 or the temperature of the heater 35.

The air-fuel ratio feedback control performed by the engine control microcomputer 16 is not the essence of the invention and may be implemented with know techniques. The explanation thereof in brief will thus be made here. The engine control microcomputer 16 monitors outputs from the A/F sensor 30 and other sensors (not shown) and performs wider range and narrower range air-fuel ratio feedback control selectively. In the wider range air-fuel ratio feedback control, the air-fuel ratio of mixture supplied to the engine 10 is controlled over a wider air-fuel ratio range embracing a lean mixture range using the so-called modern control or PI control algorithm. In the narrower range air-fuel ratio control, the air-fuel ratio of mixture is controlled so that it may reach a target value within a narrower air-fuel ratio range around the stoichiometric air-fuel ratio.

Figure 2A:
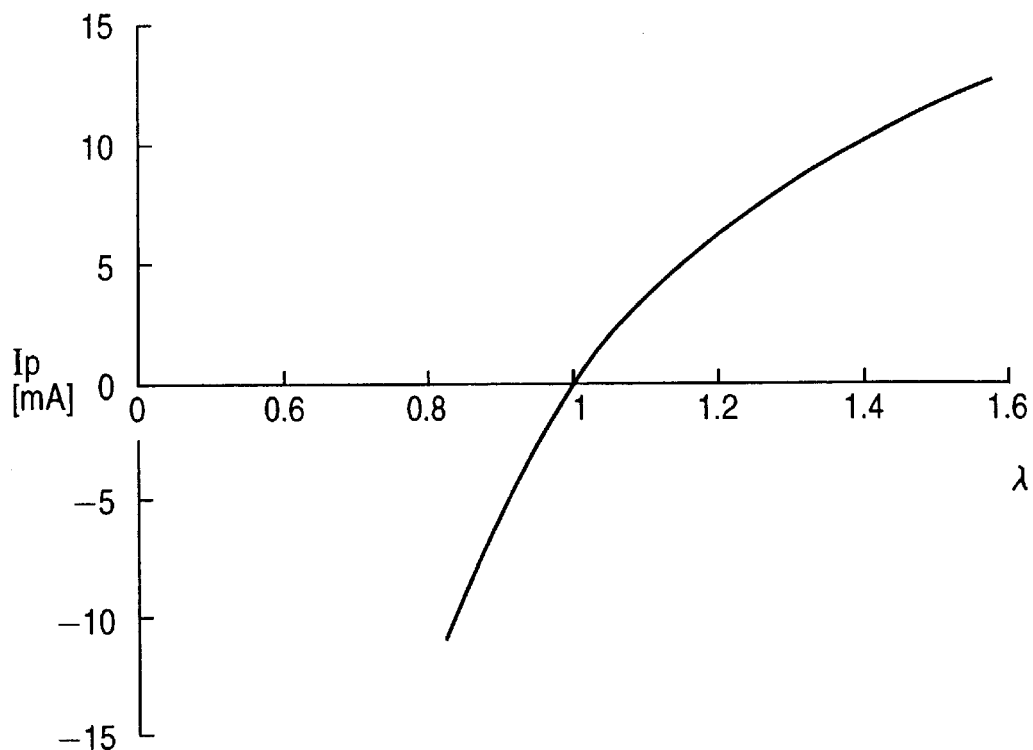
FIG. 2(a) is a graph which shows a relation between an air-fuel ratio of mixture supplied to an engine and an output current of a gas concentration sensor.
Figure 2B:
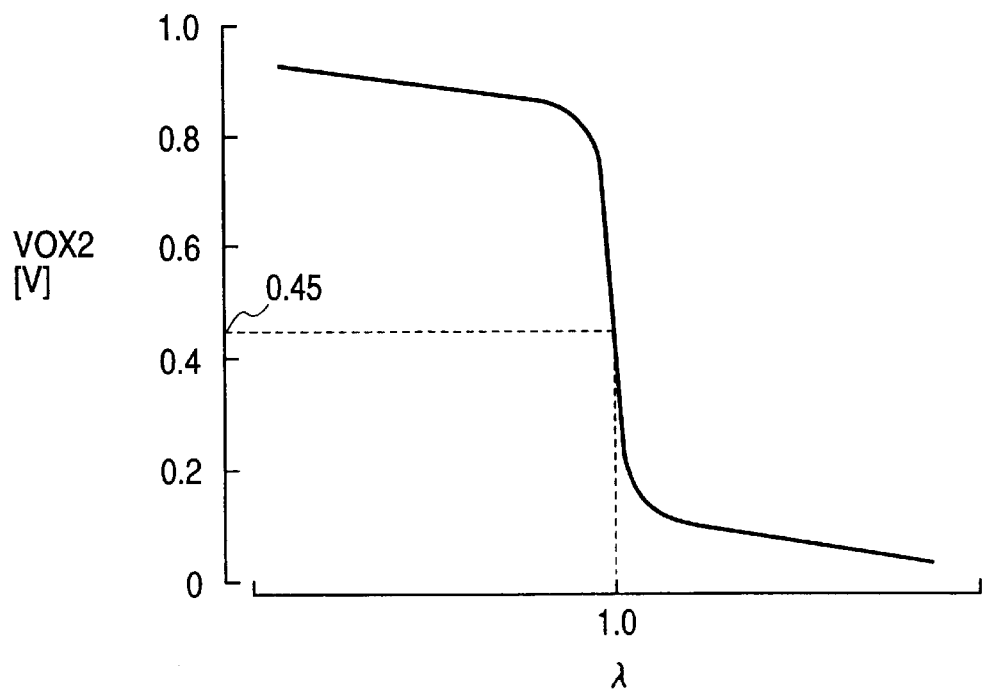
FIG. 2(b) is a graph which shows a relation between an air-fuel ratio of mixture near a stoichiometric air-fuel ratio and an output voltage of a gas concentration sensor.

The A/F sensor 30 has output characteristics, as shown in FIGS. 2(a) and 2(b). Specifically, when the engine control microcomputer 16 starts performing the wider range air-fuel ratio feedback control, the air-fuel ratio measuring microcomputer 20 applies the voltage to the A/F sensor 30 through the bias control circuit 40. The A/F sensor 30 produces a limiting current signal Ip, as shown in FIG. 2(a), which changes with a change in the air-fuel ratio of mixture supplied to the engine 10. Alternatively, when the engine control microcomputer 16 starts performing the narrower range air-fuel ratio feedback control, the air-fuel ratio measuring microcomputer 20 stops the bias control circuit 40 from applying the voltage to the A/F sensor 30. The A/F sensor 30 produces an electromotive force voltage signal VOX2, as shown in FIG. 2(b), whose level changes greatly at the time the air-fuel ratio passes across the stoichiometric air-fuel ratio, that is, which indicates whether the air-fuel ratio of mixture is on the rich side or lean side. The electromotive force voltage signal VOX2 is picked up by the electromotive force measuring circuit 55 and used in the narrower range air-fuel ratio feedback control in which the air-fuel ratio of mixture supplied to the engine 10 is adjusted to the stoichiometric air-fuel ratio.

Specifically, when applied with the voltage during the wider range air-fuel ratio feedback control, the A/F sensor 30 outputs the limiting current Ip (mA) which changes, as shown in FIG. 2(a), as a function of the air-fuel ratio $\lambda$. As the air-fuel ratio is shifted to the lean side, the limiting current Ip increases, while as the air-fuel ratio is shifted to the rich side, the limiting current Ip decreases. When applied with no voltage during the narrower range air-fuel ratio feedback control, the A/F sensor 30 outputs the voltage signal VOX2 (V) whose level changes greatly immediately when the air-fuel ratio passes across the stoichiometric air-fuel ratio $\lambda=1$. The voltage signal VOX2 is provided by an electromotive force generated as a function of a difference between the concentration of oxygen in the air and the concentration of oxygen in exhaust gasses of the engine 10 and has a voltage level of approximately 1 V on the rich side and a voltage level of approximately 0 V on the lean side.

The engine control microcomputer 16 may also perform the narrower range air-fuel ratio control using the limiting current Ip outputted from the A/F sensor 30.

Figure 4:
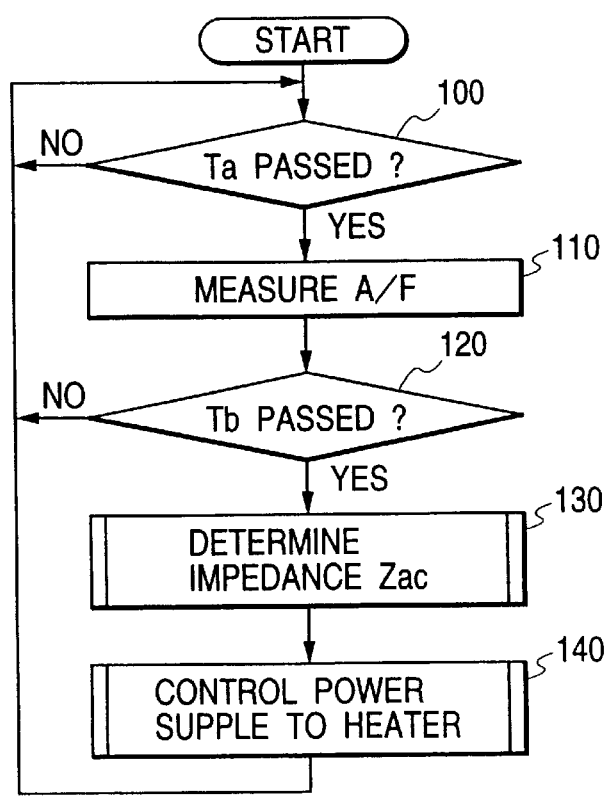
FIG. 4 is a flowchart of a main program performed in a gas sensor control system to control a power supply to a heater installed in a gas concentration sensor.

FIG. 4 shows a main program executed in a cycle by the air-fuel ratio measuring microcomputer 20 to control an electric power supply to the heater 35 of the A/F sensor 30. In this embodiment, as a resistance value of the A/F sensor 30, an AC sensor element impedance Zac, as will be described in detail later, is measured using a sweep method.

After entering the program, the routine proceeds to step 100 wherein it is determined whether a preselected period of time Ta has passed after previous measurement of the air-fuel ratio or not. The preselected period of time Ta corresponds to a measurement cycle of the air-fuel ratio and is, for example, 4 ms. If a NO answer is obtained in step 100, then the routine repeats step 100. Alternatively, if a YES answer is obtained, then the routine proceeds to step 110 for measuring the air-fuel ratio.

Figure 3:
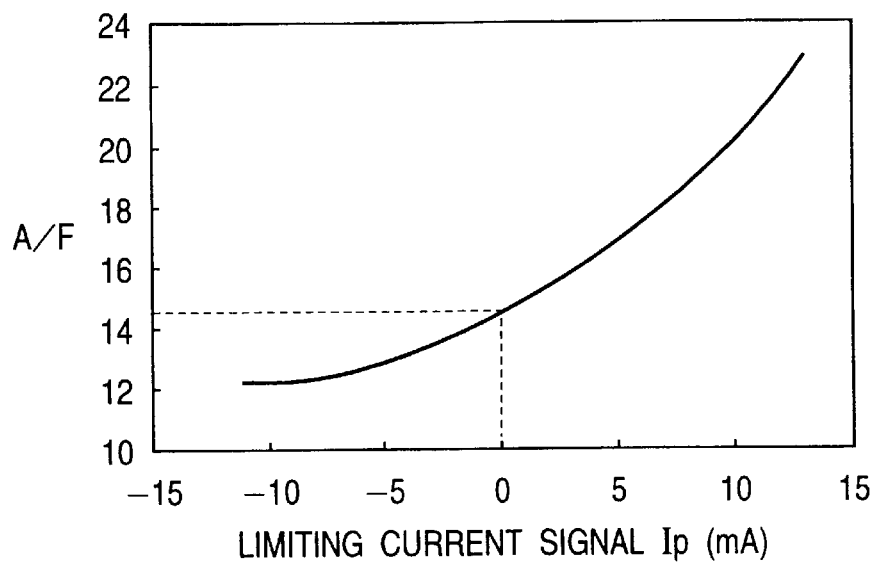
FIG. 3 is a map which is used to determine an air-fuel ratio of mixture supplied to an engine as a function of an output current of a gas concentration sensor.

In step 110, the air-fuel ratio measurement microcomputer 20 applies the voltage to the A/F sensor 30 and measures the current flowing through the solid electrolyte body 31, that is, the limiting current signal Ip through the current measuring circuit 50 to determine an input voltage as a function of the limiting current Ip and apply it across the electrodes 33 and 34 of the A/F sensor 30 for measurement of the limiting current Ip in a following air-fuel ratio measurement cycle (i.e., a following program execution cycle). The air-fuel ratio measurement microcomputer 20 converts the limiting current Ip into a corresponding air-fuel ratio by look-up using a current-A/F ratio map, as shown in FIG. 3, and outputs it to the engine control microcomputer 16.

The routine proceeds to step 120 wherein it is determined whether a preselected period of time Tb has passed or not since the sensor element impedance Zac, as will be discussed later in detail, was measured previously. The preselected period of time Tb corresponds to a measurement cycle of the sensor element impedance Zac and is determined depending upon, for example, operating conditions of the engine 10. In this embodiment, when the engine 10 is in a normal operating condition in which a change in air-fuel ratio is relatively small, Tb=2 sec. When the engine 10 is in a start-up and transient conditions in which the air-fuel ratio changes greatly, Tb=128 msec.

If a YES answer is obtained in step 120, then the routine proceeds to step 130 wherein the sensor element impedance Zac is determined. The routine proceeds to step 140 wherein a power supply to the heater 35 is controlled. Alternatively, if a NO answer is obtained in step 120, then the routine returns back to step 100. The operations in step 120 and 130 will be discussed in detail below with reference to FIGS. 5 and 6, respectively.

Figure 5:
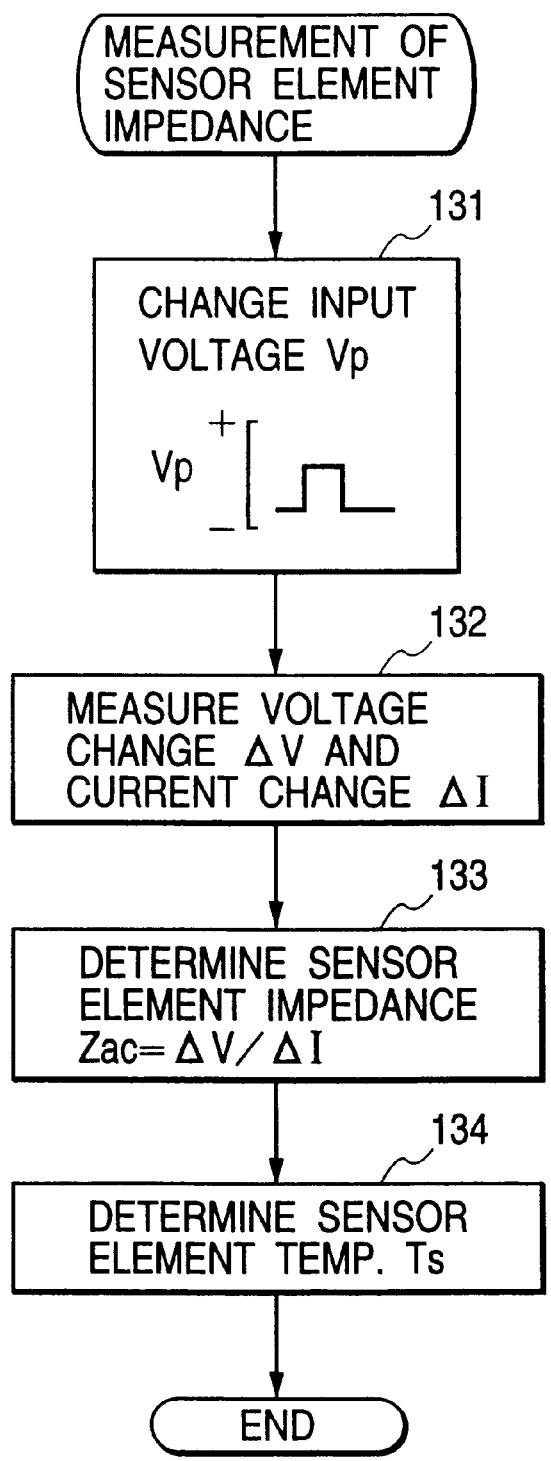
FIG. 5 is a flowchart of a subprogram used to determine an AC impedance of a sensor element of a gas concentration sensor.

After entering step 130, the routine proceeds to step 131 shown in FIG. 5 wherein the output of the bias command signal Vr is controlled to change a voltage Vp now provided to the A/F sensor 30 instantaneously to the positive side, thereby applying a sensor element impedance measuring voltage to the A/F sensor 30. The applied duration of the sensor element impedance measuring voltage is several tens to one hundred $\mu$sec. in light of frequency characteristics of the A/F sensor 30. Subsequently, the routine proceeds to step 132 wherein a change $\Delta V$ in voltage Vp and a change $\Delta I$ in sensor current measured by the current measuring circuit 50 are determined. The routine proceeds to step 133 wherein the sensor element impedance Zac is calculated using the voltage change $\Delta V$ and the current change $\Delta I$ according to the relation of Zac=$\Delta V/\Delta I$.

The routine proceeds to step 134 wherein a sensor element Temperature Ts is determined based on the sensor element impedance Zac by look-up using a map, as shown in FIG. 9, which shows that as the sensor element temperature Ts decreases, the sensor element impedance Zac increases greatly.

The measurement of the sensor element impedance Zac is, as discussed above, achieved by elevating the voltage applied to the A/F sensor 30 instantaneously, as shown in FIG. 8(a), to produce the sensor element impedance measuring voltage having a given time constant. After a lapse of a time t, as shown in FIG. 8(b), following application of the sensor element impedance measuring voltage to the A/F sensor 30, the peak of a current output from the A/F sensor 30 appears. This rise in the current output is measured as the current change $\Delta I$ and used to determine the sensor element impedance Zac together with the voltage change $\Delta V$. The application of the sensor element impedance measuring voltage to the A/F sensor 30 is accomplished through the low-pass filter 22 and the bias control circuit 40, thereby avoiding an excessive rise in the current output from the A/F sensor 30, which results in improved measurement accuracy of the sensor element impedance Zac.

The control of power supply to the heater 35 performed in step 140 in FIG. 4 will be described below with reference to FIG. 6.

Figure 6:
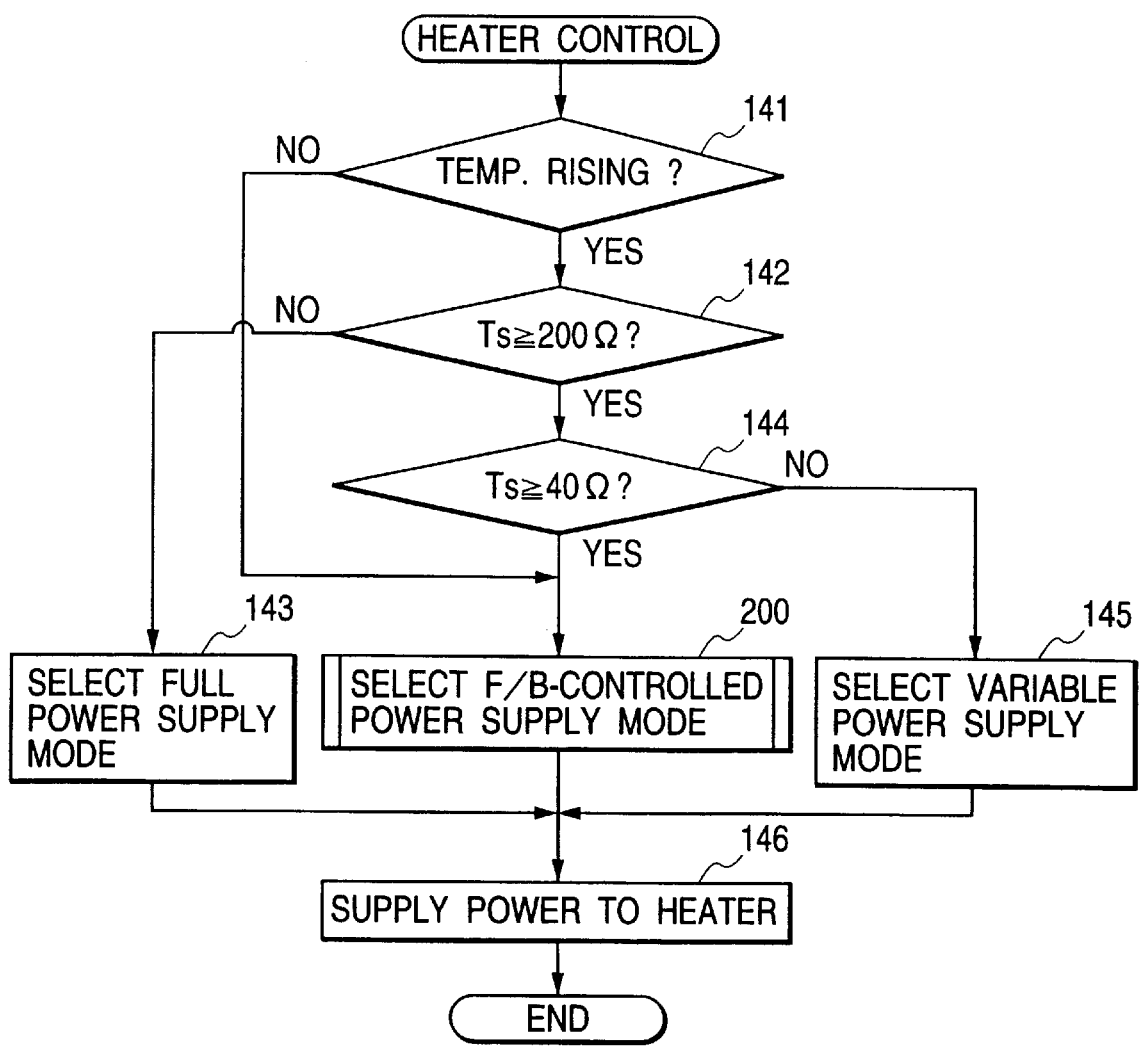
FIG. 6 is a flowchart of a subprogram used to control a power supply to a heater installed in a gas concentration sensor.

After entering step 140, the routine proceeds to step 141, as shown in FIG. 6, wherein it is determined whether the temperature of the engine 10 is rising after start-up of the engine 10 or not. If a YES answer is obtained, then the routine proceeds to step 142 wherein it is determined whether the sensor element temperature Ts determined in step 134 is greater than a given value (equivalent to the sensor element impedance of 200 $\Omega$) or not which indicates a semi-active state of the sensor element (i.e., the solid electrolyte body 31). If the engine 10 is still in a warm-up mode, a NO answer is obtained in step 142, and the routine proceeds to step 143 wherein a full power supply mode is selected. The routine proceeds to step 146 wherein a duty factor-controlled signal DUTY inputted from the heater control circuit 25 to the heater 35 is kept in duty factor at 100% to supply the power to the heater 35 fully. The routine then returns back to the main program in FIG. 4.

If the duty factor of the duty factor-controlled signal DUTY to the heater 35 is kept at 100%, and the solid electrolyte body 31 of the A/F sensor 30 is heated by the heater 35 so that the sensor element temperature Ts exceeds the given value, a YES answer is obtained in step 142. The routine, thus, proceeds to step 144 wherein it is determined whether the sensor element temperature Ts is greater than a given value (equivalent to the sensor element impedance of 40 Ω) or not which indicates the need for the feedback control of the sensor element temperature Ts.

If a NO answer is obtained meaning that the A/F sensor 30 is not yet brought into an active state, then the routine proceeds to step 145 wherein a variable power supply mode is selected. In the variable power supply mode, the duty factor-controlled signal DUTY inputted to the heater 35 is determined so that a greater power is supplied to the heater 35 when the sensor element temperature Ts is lower, that is, when the sensor element impedance Zac is greater. The routine proceeds to step 146 wherein the power supply to the heater 35 is controlled based on the duty factor-controlled signal DUTY determined in step 145.

Figure 7:
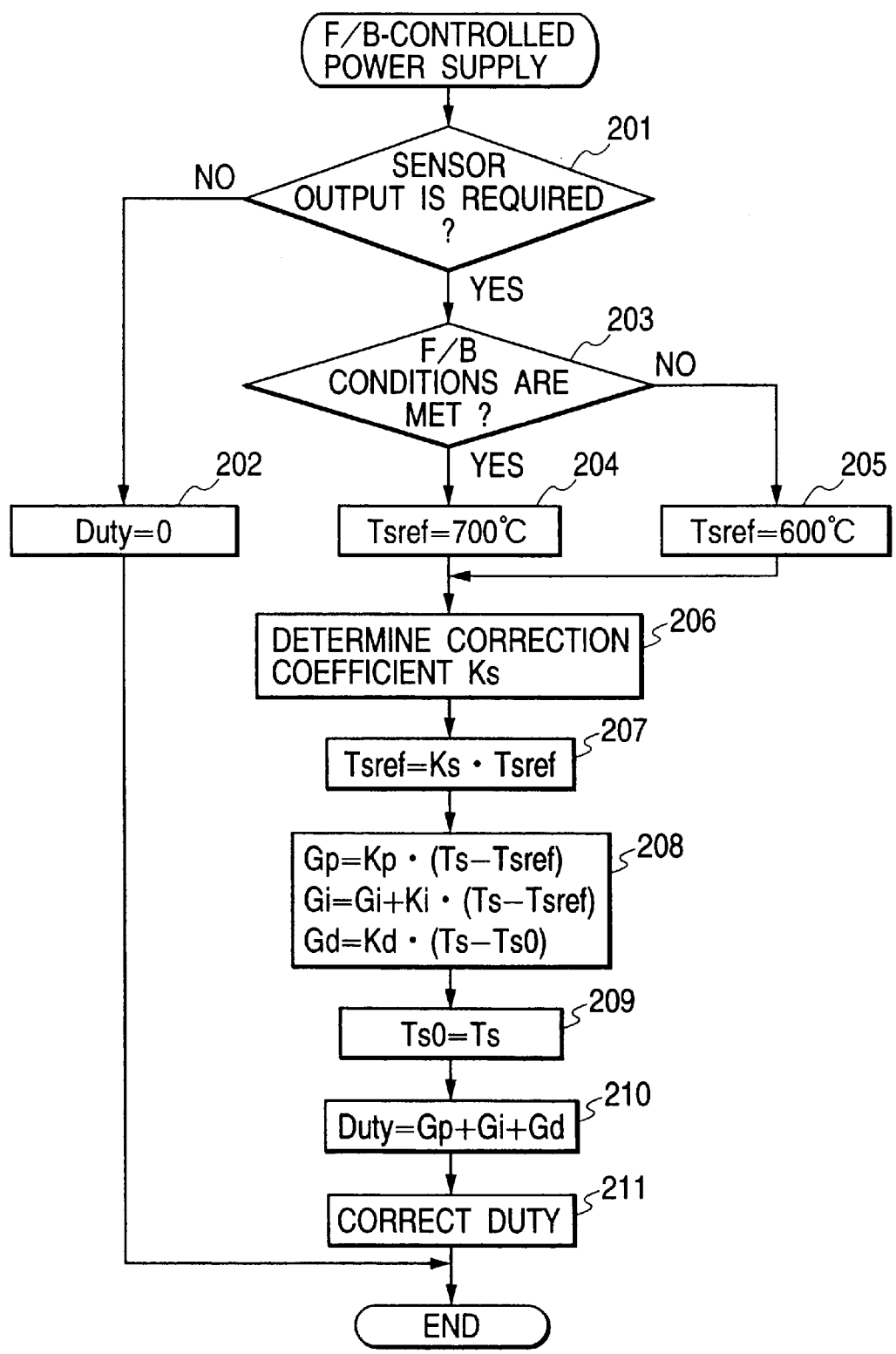
FIG. 7 is a flowchart of a subprogram to determine a target value of a controlled temperature of a heater installed in a gas concentration sensor.

If the A/F sensor 30 has been activated completely, and the sensor element temperature Ts exceeds the given value in step 144, then a YES answer is obtained. The routine, thus, proceeds to step 200 wherein a feedback-controlled power supply mode, as will be discussed later in detail with reference to FIG. 7, is selected to determine the duty factor-controlled signal DUTY to be inputted to the heater 35. The routine proceeds to step 146 wherein the power supply to the heater 35 is controlled based on the duty factor-controlled signal DUTY determined in step 200.

Upon completion of warming up of the engine 10, a NO answer is obtained in step 141, and the routine proceeds directly to step 200.

FIG. 7 shows the feedback-controlled power supply to the heater 35 performed in step 200 in FIG. 6.

First, in step 201, it is determined whether an output of the A/F 30 sensor is to be used in the ECU 15 or not. For instance, if the engine 10 is at rest or any failure is occurring in the air-fuel ratio control system, so that the feedback control of the air-fuel ratio is stopped, a NO answer is obtained, and the routine proceeds to step 202 wherein the duty factor-controlled signal DUTY is set to zero (i.e., duty factor=0%) to cut the power supply to the heater 35. The routine then returns back to the program in FIG. 6. In step 202, the duty factor of the duty factor-controlled signal DUTY may be set to a smaller value and not zero to supply a small quantity of power to the heater 35.

Alternatively, if a YES answer is obtained in step 201, then the routine proceeds to step 203 wherein all or at least one, as the case may be, of feedback control execution conditions, as listed below, is met or not.

(1) The temperature of a coolant of the engine 10 is greater than, for example, 40° C.

(2) The engine 10 is not in high load and high speed conditions.

(3) The engine 10 is not undergoing a fuel cut.

The determination in step 203 is made using data on engine operating conditions derived in the engine control microcomputer 16.

If a YES answer is obtained in step 203, then the routine proceeds to step 204 wherein a target temperature value Tsref is set to 700° C. Alternatively, if a NO answer is obtained, then the routine proceeds to step 205 wherein the target temperature value Tsref is set to 600° C. Specifically, if the YES answer is obtained in step 203 meaning that the air-fuel ratio feedback control requires an output of the A/F sensor 30, the target temperature value Tsref is set to a thermal activation point (i.e., 700° C.) required to keep the A/F sensor 30 activated in step 204. Alternatively, if the NO answer is obtained in step 203 meaning that the output of the A/F sensor 30 needs not be used in the air-fuel ratio control, the A/F sensor 30 is allowed to be in an inactive state. The target temperature value Tsref is, thus, set to a temperature lower than the thermal activation point, thereby minimizing the power consumed by the heater 35, which will result in a decrease in fuel consumption of the engine 10. For instance, when the target temperature value Tsref is set to 700° C., the heater 35 consumes about 14.5W, while when the target temperature value Tsref is set to 600° C., the heater 35 consumes about 8.5W, which results in a decrease in power consumption of about 6W.

Figure 10:
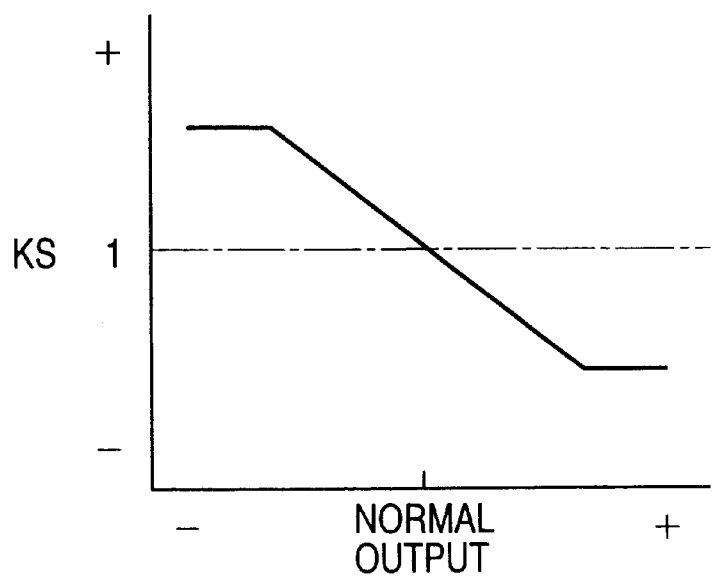
FIG. 10 is a map which shows a relation between an output of a gas concentration sensor and a deterioration correction coefficient.

After step 204 or 205, the routine proceeds to step 206 wherein a deterioration correction coefficient Ks is determined as a function of the degree of deterioration of the A/F sensor 30 by look-up using a map as shown in FIG. 10. The routine proceeds to step 207 wherein the target temperature value Tsref is corrected using the deterioration correction coefficient Ks (Tsref=Ks·Tsref). For instance, if the deterioration of the A/F sensor 30 causes an output of the A/F sensor 30 to show a value greater than a normal value, the deterioration correction coefficient Ks is set smaller than one (Ks<1) to decrease the target temperature value Tsref. Alternatively, if the deterioration of the A/F sensor 30 causes the output of the A/F sensor 30 to show a value smaller than the normal value, the deterioration correction coefficient Ks is set greater than one (Ks>1) to increase the target temperature value Tsref.

The routine proceeds to step 208 wherein the duty factor-controlled signal DUTY is determined in a manner, as described below, for bringing the sensor element temperature Ts into agreement with the target temperature value Tsref under feedback control. As one example to determine the duty factor-controlled signal DUTY, this embodiment uses the so-called PID control. Of course, the PI control or the P control may alternatively be used.

First, a proportional term Gp, an integral term Gi, and a differential term Gd are determined by the following relations.

$$Gp = Kp \cdot (Ts - Tsref)$$

$$Gi = Gi + Ki \cdot (Ts - Tsref)$$

$$Gd = Kd \cdot (Ts - Ts0)$$

where Kp is a proportional constant, Ki is an integral constant, Kd is a differential constant, and Ts0 is the sensor element temperature Ts determined in a previous program execution cycle.

The routine proceeds to step 209 wherein the sensor element temperature Ts determined in this program execution cycle is defined as Ts0.

The routine proceeds to step 210 wherein the proportional term Gp, the integral term Gi, and the differential term Gd are summed up to determine the duty factor-controlled signal DUTY (DUTY=Gp+Gi+Gd).

Figure 11:
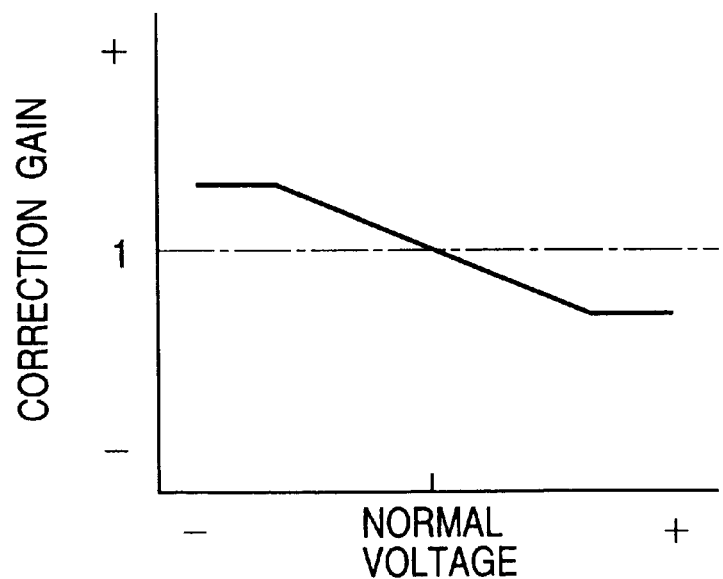
FIG. 11 is a map which shows a relation between a correction gain and an output of a battery.

The routine proceeds to step 211 wherein the duty factor-controlled signal DUTY is corrected as a function of an output voltage of a battery installed in the vehicle (i.e., the voltage of a power source of the air-fuel ratio control system). Specifically, a correction gain is determined using a map, as shown in FIG. 11, as a function of a shift in output voltage of the battery from a normal voltage.

After step 211, the routine returns back to the program in FIG. 6.

The second embodiment will be described below.

Figure 12:
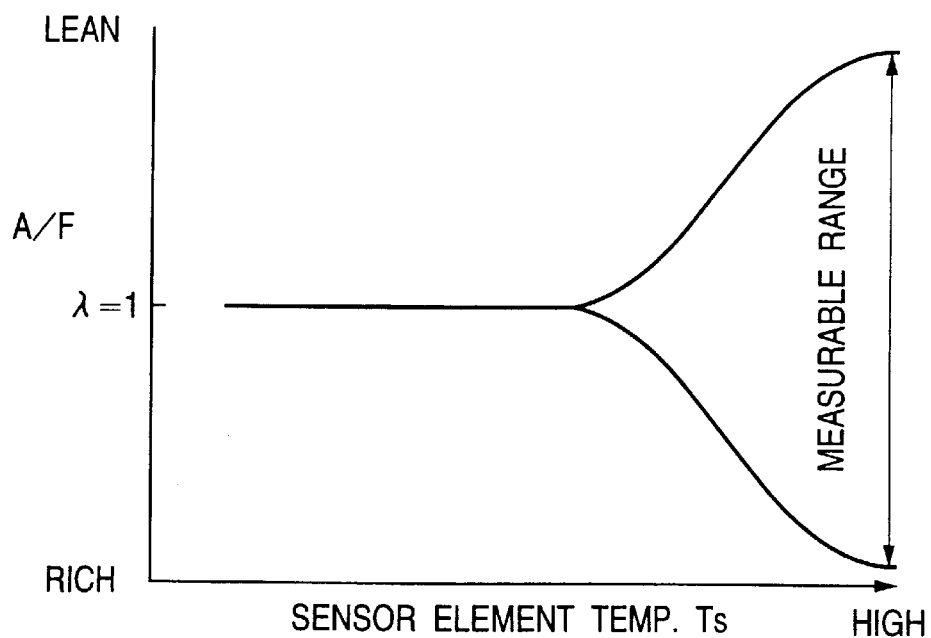
FIG. 12 is a graph which shows a relation between an air-fuel ratio measurable range and a sensor element temperature.

The sensor element temperature Ts and a measurable range of the air-fuel ratio bear a relation, as shown in FIG. 12, in which the measurable range of the air-fuel ratio expands greatly at the instant the sensor element temperature Ts exceeds a specified thermal point.

Figure 13:
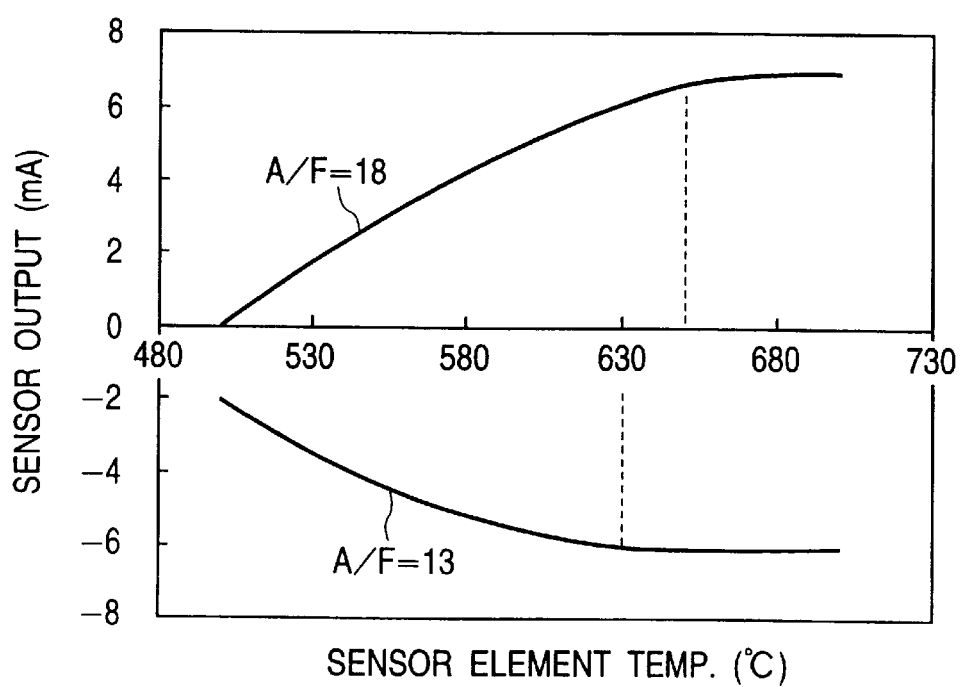
FIG. 13 is a graph which shows a relation between an output of a gas concentration sensor and a desired activating temperature of a sensor element.

Additionally, even if the air-fuel ratio is constant, an output (mA) of the A/F sensor 30 changes, as shown in FIG. 13, with a change in sensor element temperature Ts. For example, in the case of the air-fuel ratio (A/F)=18, the sensor output does not show a corresponding current value (about 7 mA) when the sensor element temperature Ts is lower than 650° C. Thus, in a sensor element temperature range less than 650° C., it is difficult to measure a lean air-fuel ratio (A/F=18) correctly. In the case of A/F=13, the sensor output does not show a corresponding current value (about −6 mA) when the sensor element temperature Ts is lower than 630° C. Thus, in a sensor element temperature range less than 630° C., it is difficult to measure a rich air-fuel ratio (A/F=13) correctly. In the case of A/F=14.7 (i.e., stoichiometric air-fuel ratio), the A/F sensor 30 is designed to output 0 mA. The sensor output, thus, dose not depend upon the sensor element temperature Ts at all.

It is, therefore, noted that the sensor element temperature Ts required for the A/F sensor 30 to provide a correct output changes with a change in air-fuel ratio of mixture supplied to the engine 10.

In light of the above fact, the second embodiment is designed to change the target temperature value Tsref as a function of a target air-fuel ratio determined by the engine control microcomputer 16.

Figure 14:
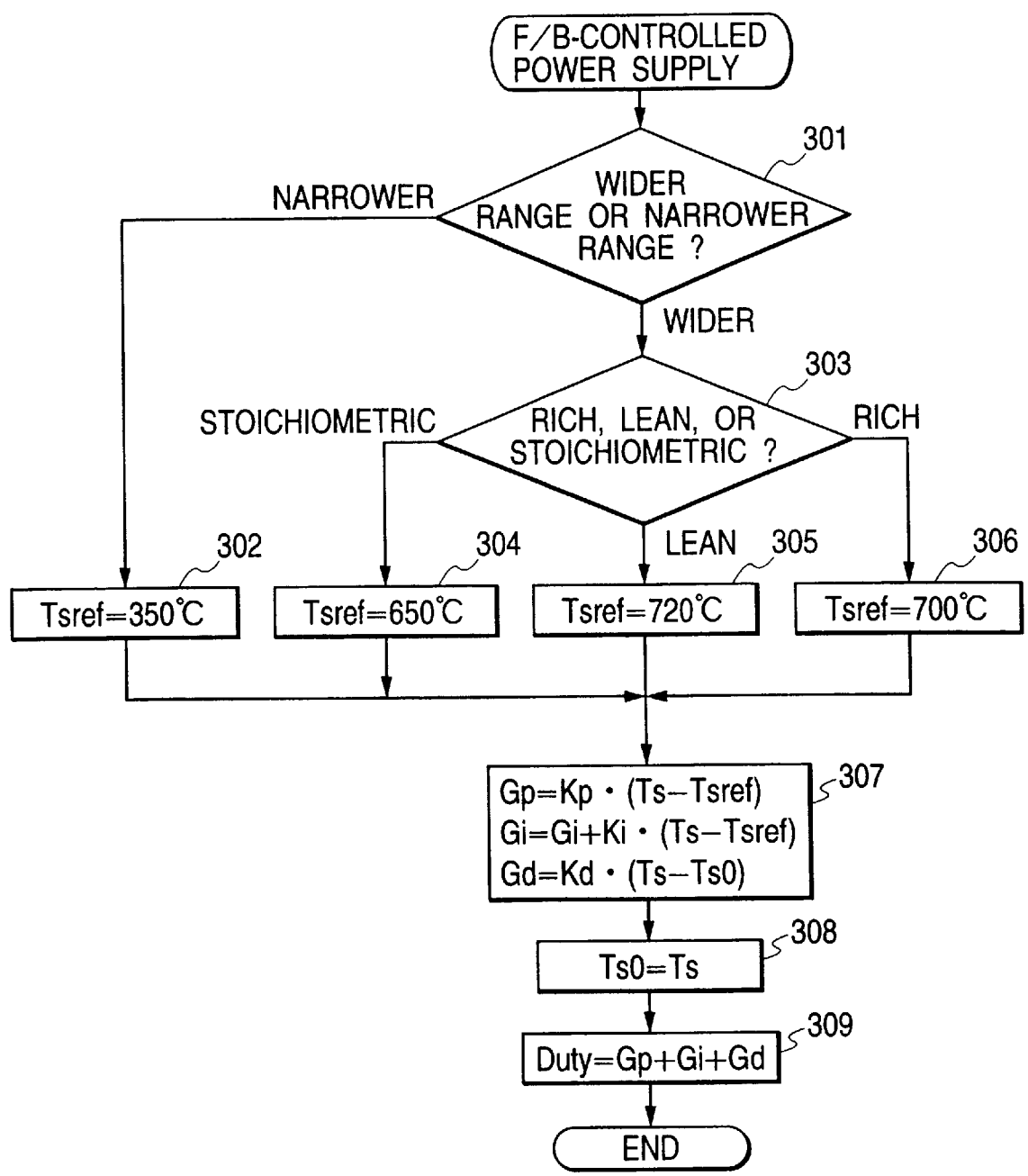
FIG. 14 is a flowchart of a subprogram to determine a target value of a controlled temperature of a heater installed in a gas concentration sensor according to the second embodiment.

FIG. 14 shows a subprogram for feedback-controlled power supply to the heater 35 according to the second embodiment performed in step 200 in FIG. 6.

After entering the program, the routine proceeds to step 301 wherein the engine control data outputted from the engine control microcomputer 16 is monitored to determine which of the wider range air-fuel ratio feedback control and the narrower range air-fuel ratio feedback control the engine control microcomputer 16 is required to perform. If it is required to perform the narrower range air-fuel ratio feedback control to adjust the air-fuel ratio of mixture supplied to the engine 10 within the narrower air-fuel ratio range near the stoichiometric air-fuel ratio ($\lambda$=1), the temperature of the sensor element, as already described, needs not be kept high, and thus the sensor element temperature Ts is allowed to be low. The routine, thus, proceeds to step 302 wherein the target temperature value Tsref is set to 350° C. Alternatively, if it is required to perform the wider range air-fuel ratio feedback control to adjust the air-fuel ratio of mixture supplied to the engine 10 over the wider air-fuel ratio range including the lean mixture range, then the routine proceeds to step 303 wherein it is determined which of the stoichiometric mixture, a lean mixture, and a rich mixture a target air-fuel ratio determined by the engine control microcomputer 16 indicates. If the target air-fuel ratio indicates the stoichiometric mixture, then the routine proceeds to step 304 wherein the target temperature value Tsref is set to 650° C. If the target air-fuel ratio indicates the lean mixture, then the routine proceeds to step 305 wherein the target temperature value Tsref is set to 720° C. If the target air-fuel ratio indicates the rich mixture, then the routine proceeds to step 306 wherein the target temperature value Tsref is set to 700° C. The target temperature value Tsref in each of steps 304 to 306 is determined based on the output-temperature relation shown in FIG. 13 and may be selected from a range in which the A/F sensor 30 provides an output required for the air-fuel ratio feedback control accurately.

After step 302, 304, 305, or 306, the routine proceeds to step 307 wherein the duty factor-controlled signal DUTY is determined in the same manner as described in step 208 in FIG. 7. Steps 307, 308 and 309 are identical with steps 208, 209, and 210, and explanation thereof in detail will be omitted here. However, in the case where the target temperature value Tsref is set to 350° C. in step 302, it becomes difficult to measure the sensor element impedance Zac, thus resulting in difficulty in determining the sensor element temperature Ts. The power supply to the heater 35 is, thus, kept constant regardless of the sensor element temperature Ts.

The same steps as steps 206, 207, and 211 may be added to correct the target temperature value Tsref as a function of the degree of deterioration of the A/F sensor 30 and a change in voltage of the battery installed in the vehicle.

The A/F sensor 30 is, as described above, so controlled as to selectively output the electromotive force voltage signal VOX2, as shown in FIG. 2(*b*), (also referred to as $O_2$ output below) whose level changes greatly depending upon whether the air-fuel ratio is on the rich or lean side in the narrower range air-fuel ratio feedback control and the limiting current signal Ip, as shown in FIG. 2(*a*), (also referred to as A/F output below) which changes linearly as a function of an air-fuel ratio in the wider range air-fuel ratio feedback control. The second embodiment may, therefore, alternatively determine in step 301 whether an output of the A/F sensor 30 is the $O_2$ output or the A/F output to change the target temperature value Tsref. If the output of the A/F sensor 30 is the A/F output, then the routine proceeds to step 303 wherein it is determined which of the stoichiometric mixture, a lean mixture, and a rich mixture the A/F output indicates. If the A/F output indicates the stoichiometric mixture, then the routine proceeds to step 304 wherein the target temperature value Tsref is set to 650° C. If the A/F output indicates the lean mixture, then the routine proceeds to step 305 wherein the target temperature value Tsref is set to 720° C. If the A/F output indicates the rich mixture, then the routine proceeds to step 306 wherein the target temperature value Tsref is set to 700° C.

Figure 15:
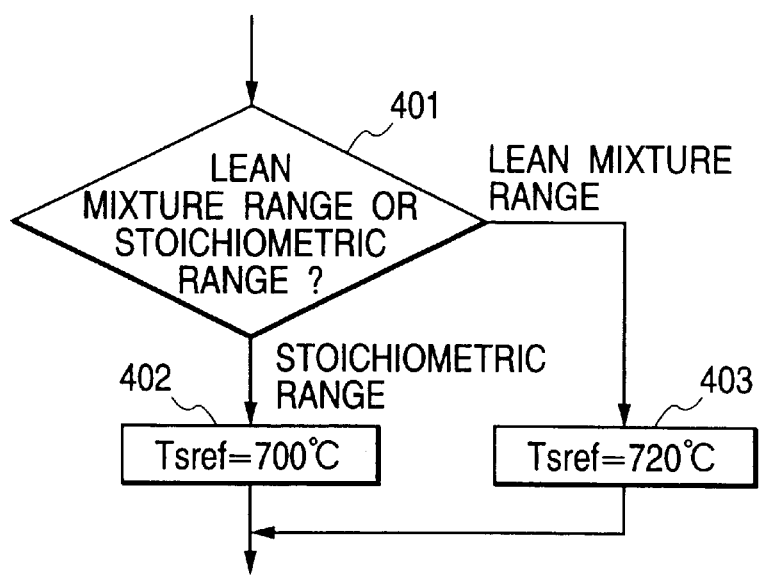
FIG. 15 is a flowchart of a subprogram to determine a target value of a controlled temperature of a heater installed in a gas concentration sensor according to the third embodiment.

FIG. 15 shows a subprogram for feedback-controlled power supply to the heater 35 according to the third embodiment of the invention which is a modification of the one shown in FIG. 14 and which is used in performing the lean burn control of the engine 10. Steps 401, 402, and 403 are executed instead of steps 303 to 306. Other steps are identical, and explanation thereof in detail will be omitted here.

In step 401, it is determined within which of a stoichiometric range and a lean mixture range the A/F output from the A/F sensor 30 lies. If it is required to perform the air-fuel feedback control using the A/F output within the stoichiometric range defined across the stoichiometric air-fuel ratio, then the routine proceeds to step 402 wherein the target temperature value Tsref is set to 700° C. Alternatively, if it is required to perform the air-fuel feedback control using the A/F output within the lean mixture range, then the routine proceeds to step 403 wherein the target temperature value Tsref is set to 720° C.

The fourth embodiment of the invention will be described below.

Figure 17:
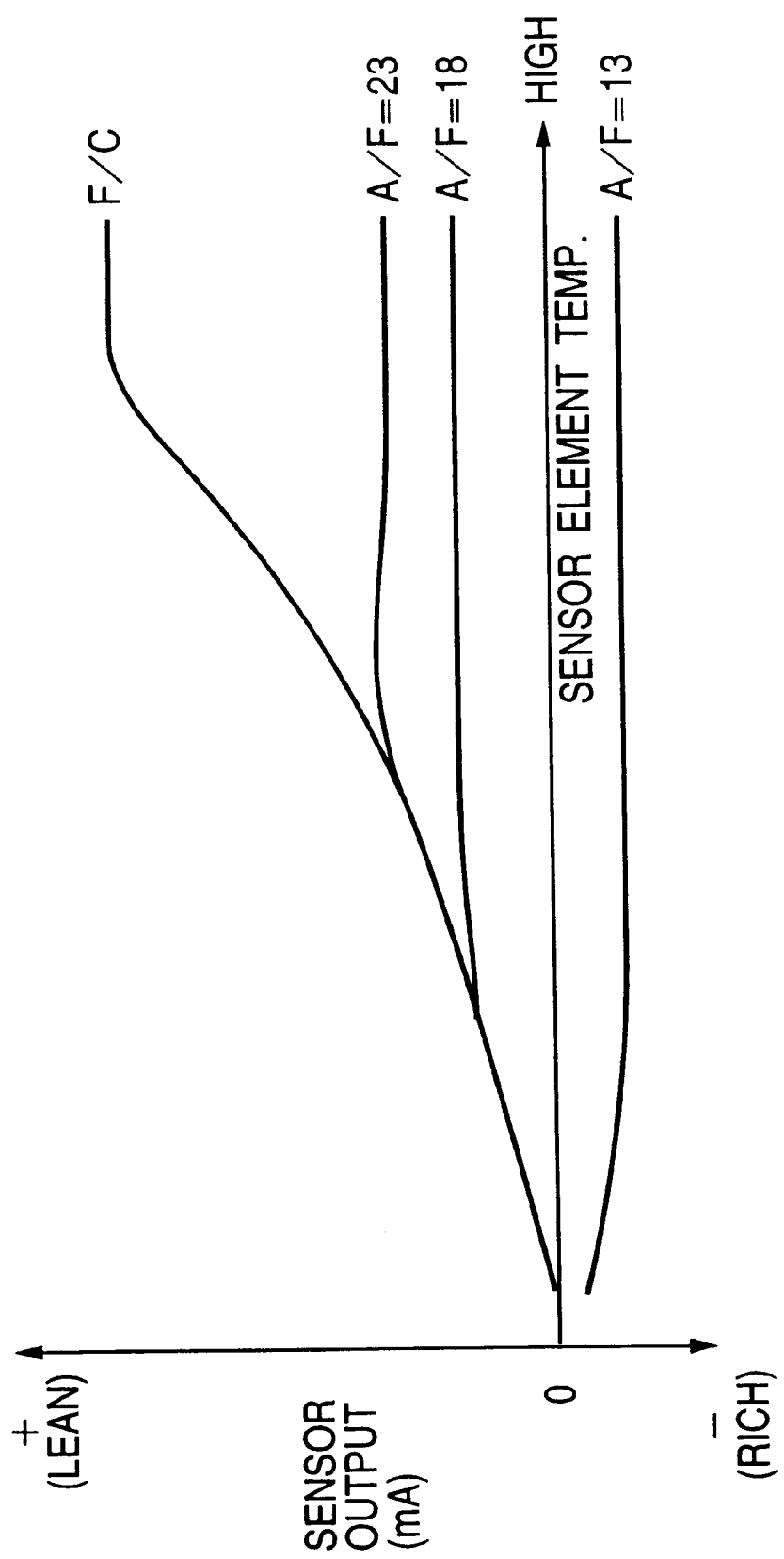
FIG. 17 is a graph which shows outputs of a gas concentration sensor for different temperature of a sensor element.

When the engine 10 undergoes a fuel cut, it will cause the A/F sensor 30 to output much limiting current indicating an extremely lean mixture or air. In this case, adjustment of the target temperature value Tsref to a corresponding one other than those determined in steps 402 and 403 in FIG. 15 is necessary to have the A/F sensor 30 provide an accurate output. Specifically, in the case of the fuel cut, it is, as shown in FIG. 17, necessary to elevate the sensor element temperature Ts of the A/F sensor 30 above the target temperature value Tsref selected in the lean mixture range.

Figure 16:
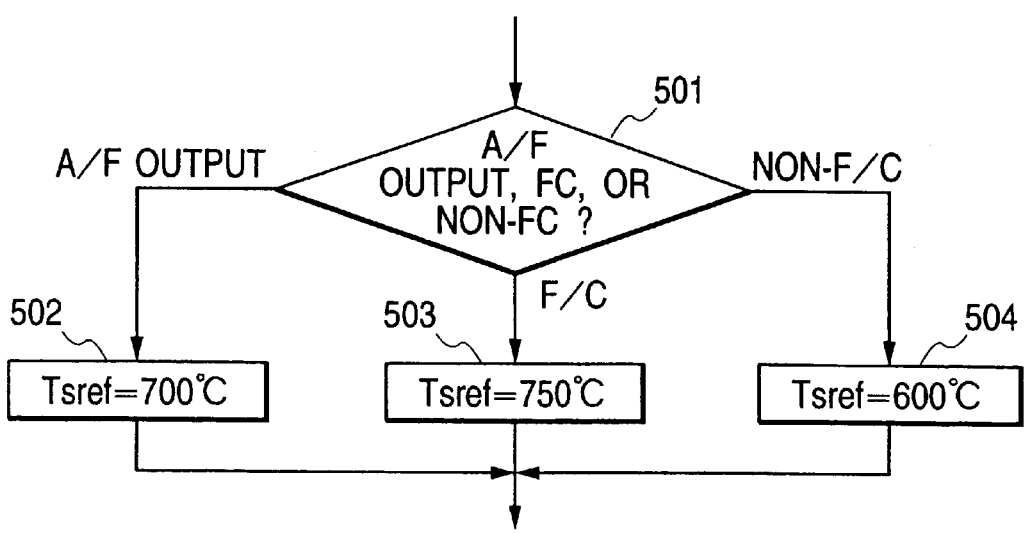
FIG. 16 is a flowchart of a subprogram to determine a target value of a controlled temperature of a heater installed in a gas concentration sensor according to the fourth embodiment.

FIG. 16 shows a subprogram for feedback-controlled power supply to the heater 35 according to the fourth embodiment which is a modification of the one shown in FIG. 15. Steps 501, 502, 503, and 504 are executed instead of steps 401, 402, and 403.

In step 501, it is determined which of an air-fuel ratio within a normal range, a fuel cut, and a non-fuel cut the output of the A/F sensor 30 indicates. If it is determined that the output of the A/F sensor 30 indicates any air-fuel ratio within the normal range, then the routine proceeds to step 502 wherein the target temperature value Tsref is set to 700° C. If it is determined that the output of the A/F sensor 30 indicates the fuel cut, then the routine proceeds to step 503 wherein the target temperature value Tsref is set to 750° C. If it is determined that the output of the A/F sensor 30 indicates the non-fuel cut, then the routine proceeds to step 504 wherein the target temperature value Tsref is set to 600° C. The non-fuel cut means the following case. When the engine 10 is undergoing a fuel cut, the A/F sensor 30, as described above, outputs much limiting current indicating an extremely lean mixture. If such a limiting current continues to be inputted to the current measuring circuit 50, it will cause circuit elements built therein to be heated up. In order to project the circuit elements from thermal damage, the bias control circuit 40 usually reduces the voltage applied to the A/F sensor 30 so as to output a current between a value (i.e., the A/F output) indicating any air-fuel ratio within the normal range and a value indicating the fuel cut. Additionally, if the output of the A/F sensor 30 has a current level exceeding a measurable range of the current measuring circuit 50, the bias control circuit 40 also reduces the voltage applied to the A/F sensor 30 similar to the above. Therefore, if it is determined in step 501 that the A/F sensor 30 outputs a current between a value indicating any air-fuel ratio within the normal range and a value indicating the fuel cut, the routine may proceeds to step 504.

The determination in step 501 may be made by monitoring the engine control data outputted from the engine control microcomputer 16. For example, if the engine control data indicates that the engine control microcomputer 16 reduces the voltage applied to the A/F sensor 30 to stop detection of the fuel cut for the above reasons, the routine may proceed to step 504.

Figure 18:
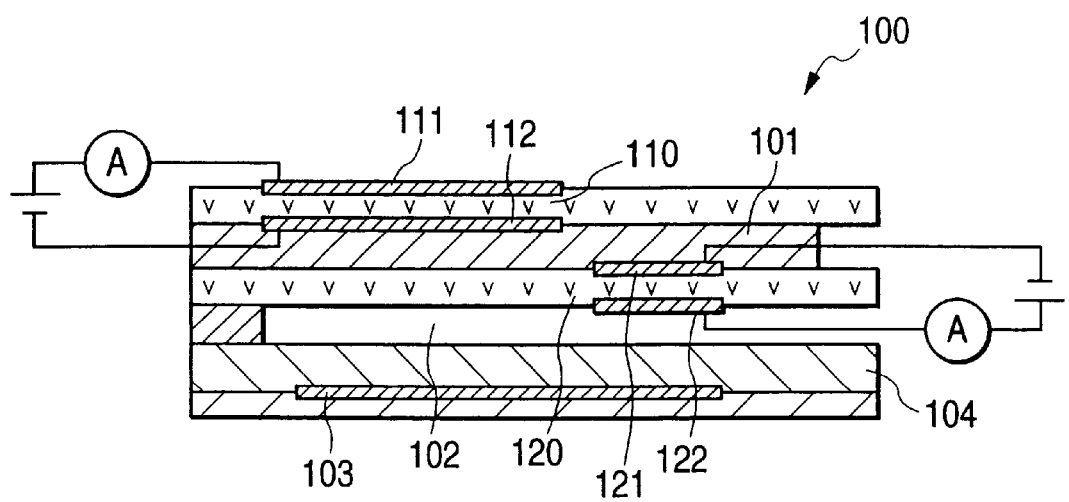
FIG. 18 is a sectional view which shows the first modification of a gas concentration sensor.

FIG. 18 shows a gas concentration sensor 100 which is designed to measure the concentrations of NOx and $O_2$ simultaneously and which may be used in the above embodiments instead of the A/F sensor 30.

The gas concentration sensor 100 has two cells: a pump cell 110 for measuring the concentration of $O_2$ and a sensor cell 120 for measuring the concentration of NOx contained in exhaust gasses of the engine 10.

The gas concentration sensor 100 also includes a porous diffused layer 101, an air duct 102, an insulating layer 104, and a heater 103 which are laminated together with the pump cell 110 and the sensor cell 120. The gas concentration sensor 100 is installed at the right side thereof, as viewed in the drawing, on the exhaust pipe 13 so as to expose upper, lower, and left surfaces to the exhaust gasses.

The pump cell 110 is disposed on the porous diffused layer 101 so that it is exposed to the exhaust gasses. A first pump electrode 111 is mounted on the upper surface of the pump cell 110. A second pump electrode 112 is mounted on the lower surface thereof facing the porous diffused layer 101. The sensor cell 120 is interposed between the porous diffused layer 101 and the air duct 102. A first sensor cell electrode 121 is attached to an upper surface thereof facing the porous diffused layer 101. A second sensor cell electrode 122 is attached to a lower surface thereof facing the air duct 102. The exhaust gasses enters the porous diffused layer 101 from the left side thereof, as viewed in the drawing, and flow in the right direction.

The pump cell 110 and the sensor cell 120 are each formed with a solid electrolyte member such as an oxygen ion conductive oxide sintered member made from $ZrO_2$, $HfO_2$, $ThO_2$, and $Bi_2O_3$ in which CaO, MgO, $Y_2O_3$, and $Yb_2O_3$ are solved as fixing agents. The porous diffused layer 101 is made of a heat-resisting inorganic matter such as alumina, magnesia, silica, spinel, and mullite.

The first pump cell electrode 111 and the first and second sensor cell electrodes 121 and 122 are each made of a noble metal with a high catalytic activity such as platinum, while the second pump electrode 112 is made of a noble metal such as Au—Pt which hardly decomposes NOx.

The heater 103 is embedded in the insulating layer 104. The insulating layer 104 defines the air duct 102 between itself and the sensor cell 120. The air duct 102 serves as a reference gas chamber into which the air is introduced outside the sensor 100. The air in the reference gas chamber is used as a reference gas in measuring the concentration of oxygen. The insulating layer 104 is made of cermet such as alumina. The heater 103 is made of platinum and cermet such as alumina and supplied with power from the heater control circuit 25 to produce the heat for activating the whole of the sensor 100.

In operation, when exhaust gasses enter the porous diffused layer 101 and are passing the pump cell 110, application of voltage to the pump cell 110 through the electrodes 111 and 112 causes the exhaust gasses to be decomposed. Since the second pump cell electrode 112 is, as described above, made of a noble metal which hardly decomposes NOx, the exhaust gasses are decomposed only into oxygen by the pump cell 110 which is, in turn, returned to the exhaust gasses from the first pump cell electrode 111, thereby causing a current to flow through the pump cell 110 as a function of the concentration of oxygen in the exhaust gasses, which is, in turn, picked up as the A/F output by the current measuring circuit 50 of the ECU 15.

The exhaust gasses are not always decomposed into the oxygen by the pump cell 110 completely. If such a condition is encountered, application of voltage to the sensor cell 120 causes the first sensor cell electrode 121 to induce reaction of oxygen remaining in the undecomposed part of the exhaust gasses with NOx in the exhaust gasses so that NOx is separated from the exhaust gasses and discharged to the air duct 102 through the second sensor cell electrode 122, thereby causing a current to flow through the sensor cell 120 as a function of the concentration of NOx, which is, in turn, picked up by the current measuring circuit 50. Note that the gas concentration sensor 100 is, like the A/F sensor 30, operable to produce the $O_2$ output.

Figure 19:
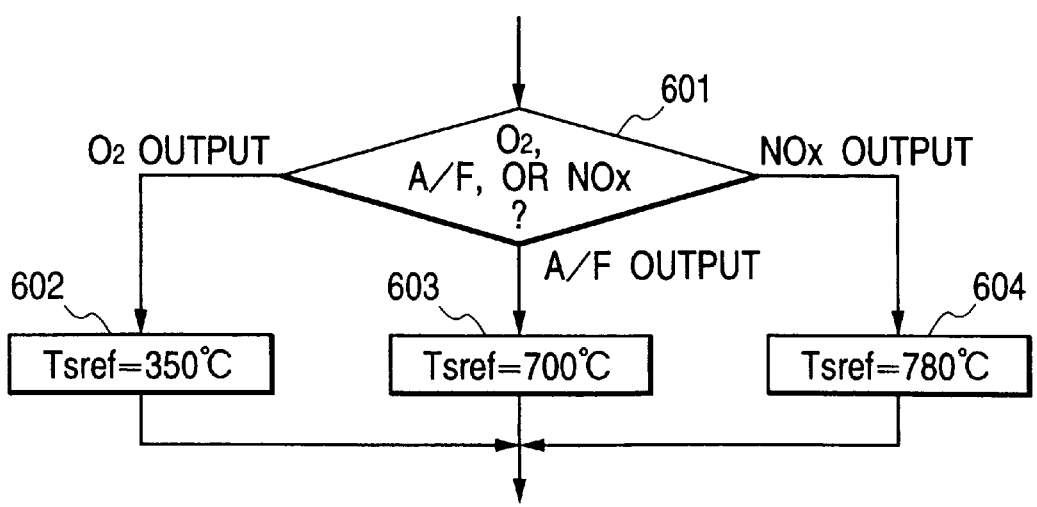
FIG. 19 is a flowchart of a subprogram to determine a target value of a controlled temperature of a heater installed in a gas concentration sensor according to the fifth embodiment.

FIG. 19 shows a subprogram for feedback-controlled power supply to the heater 103 of the gas concentration sensor 100 according to the fifth embodiment of the invention which is a modification of the one shown in FIG. 14. Steps 601, 602, 603, and 604 are executed instead of steps 301 to 306.

In step 601, it is determined which of the $O_2$ output, the A/F output, and the NOx output the engine control microcomputer 16 requires. If it is determined that the engine control microcomputer 16 requires the $O_2$ output for the narrower range air-fuel ratio feedback control, then the routine proceeds to step 602 wherein the target temperature value Tsref is set to 350° C. If it is determined that the engine control microcomputer 16 requires the A/F output for the wider range air-fuel ratio feedback control, then the routine proceeds to step 603 wherein the target temperature value Tsref is set to 700° C. If it is determined that the engine control microcomputer 16 requires the NOx output, for example, for controlling the air-fuel ratio of mixture as a function of NOx contained in the exhaust gasses, then the routine proceeds to step 604 wherein the target temperature value Tsref is set to 780° C. However, if the A/F output and the NOx output are required simultaneously, the target temperature value Tsref is set to a higher one of the sensor element temperature target values Tsref (i.e., 780° C.).

The determination in step 601 may alternatively be made by monitoring an output from the gas concentration sensor 100. Specifically, if it is determined that the gas concentration sensor 100 produces the $O_2$ output, then the routine proceeds to step 602 wherein the target temperature value Tsref is set to 350° C. If it is determined that the gas concentration sensor 100 produces the A/F output, then the routine proceeds to step 603 wherein the target temperature value Tsref is set to 700° C. If it is determined that the gas concentration sensor 100 produces the NOx output, then the routine proceeds to step 604 wherein the target temperature value Tsref is set to 780° C.

Figure 20:
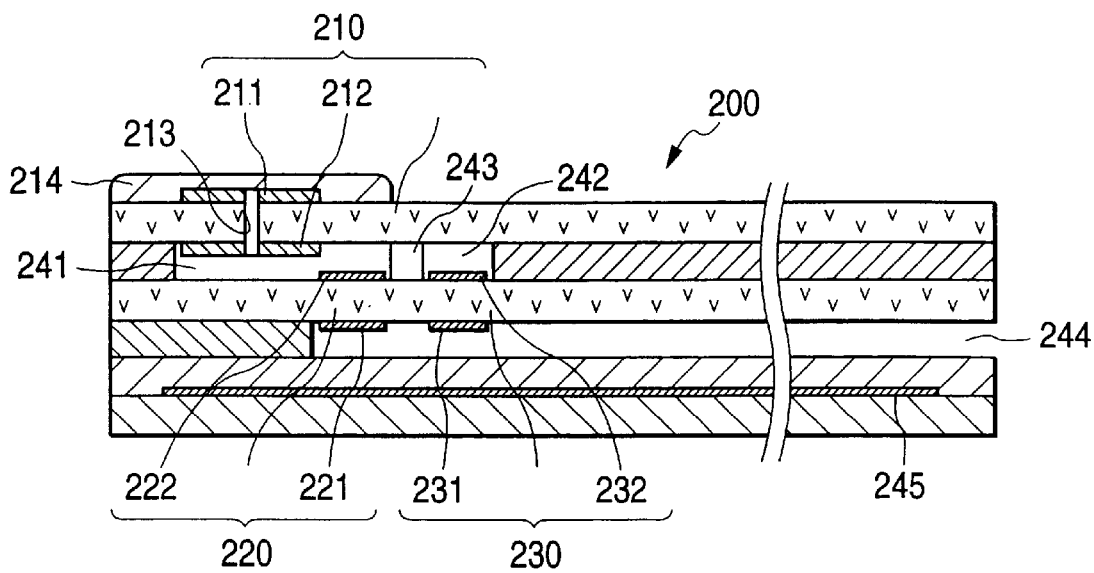
FIG. 20 is a sectional view which shows the second modification of a gas concentration sensor.

FIG. 20 shows a gas concentration sensor 200 which is a modification of the one shown in FIG. 18 and has a three-cell structure. The gas concentration sensor 200 may be employed in the above embodiments instead of the A/F sensor 30.

The gas concentration sensor 200 includes an oxygen pump cell 210, an oxygen sensor cell 220, and a NOx sensor cell 230. The oxygen pump cell 210 consists of a solid electrolyte body 219 and a pair of electrodes 211 and 212 disposed on opposed surfaces of the solid electrolyte body 219. A pin hole 213 is formed through the solid electrolyte body SEA and the electrodes 211 and 212. A porous protective layer 214 is formed over the electrode 211.

The oxygen sensor cell 220 consists of a solid electrolyte body 229 and a pair of electrodes 221 and 222 disposed on opposed surfaces of the solid electrolyte body 229. The electrode 221 is made of, for example, a porous Pt. The electrode 222, like the electrode 212 of the oxygen pump cell 210, has an electrode activity adjusted to be inactive in reduction of NOx yet active in reduction of $O_2$.

The NOx sensor cell 230 consists of the solid electrolyte body 229 common to the oxygen sensor cell 220 and a pair of electrodes 231 and 232 disposed adjacent the electrodes 221 and 222, respectively. The electrode 231 is made of a porous Pt. The electrode 232 is made of a material such as a porous Pt which is active in reduction of NOx.

First and second chambers 241 and 242 are formed between the solid electrolyte bodies 219 and 229 in communication with each other through a hole 243. An air path 244 is formed between the solid electrolyte body 229 and an insulating layer 204 in communication with the atmosphere. A heater 245 is mounted in the insulating layer 204.

The exhaust gasses enters the first chamber 241 through the pin hole 213, which causes an electromotive force to be produced in the oxygen sensor cell 220 by a difference between concentrations of oxygen to which the electrodes 221 and 222 are exposed. The electromotive force is outputted to the ECU 15 as indicating the concentration of oxygen in the first chamber 241.

When the voltage is applied to the electrodes 211 and 212 of the oxygen pump cell 210, it will cause oxygen to be drawn into and discharged from the first chamber 241 so that the oxygen in the first chamber 241 is adjusted in concentration to a constant lower value. The power supply to the oxygen pump cell 210 is so adjusted under feedback control that the electromotive force generated across the electrodes 221 and 222 of the oxygen sensor cell 220 shows a given constant value. Since the electrode 212 of the oxygen sensor cells 220 within the first chamber 241 is, as described above, inactive in reduction of NOx, the gasses in the first chamber 241 is not decomposed into NOx so that the quantity of NOx in the first chamber 241 is kept constant.

The exhaust gasses in which the concentration of oxygen is adjusted to the constant lower value by the oxygen pump cell 210 and the oxygen sensor cell 220 pass through the hole 243 and enter the second chamber 242. Since the electrode 232 of the NOx sensor cell 230 within the second chamber 242 is, as described above, active in reduction of NOx, application of voltage to the electrodes 231 and 232 of the NOx sensor cell 230 causes the exhaust gasses on the electrode 232 to be decomposed into NOx, thereby causing an oxygen ion current to flow through the electrode 232, which is, in turn, outputted to the ECU 15 as indicating the concentration of NOx.

The power supply to the heater 245 may be controlled by the ECU 15 according to the same program as one of the programs shown in FIGS. 7, 14, 115, 16, and 19 to realize the power saving without sacrificing the measurement accuracy of the gas concentration sensor 200.

The sixth embodiment will be described below in which a gas sensor control system of the invention is used in hybrid vehicles which are usually broken down into two types: one of which is a parallel hybrid vehicle having mounted thereon an internal combustion engine and an electric generator-motor both operating as a power source for driving the vehicle, and the second being a series hybrid vehicle which drives an electric generator-motor using an internal combustion engine. In this embodiment, it is assumed that the A/F sensor 30 is, as shown in FIG. 1, installed in the exhaust pipe 13 and that an output of the A/F sensor 30 is used in the ECU 15 for feedback control of the air-fuel ratio of mixture supplied to the engine 10.

Figure 21:
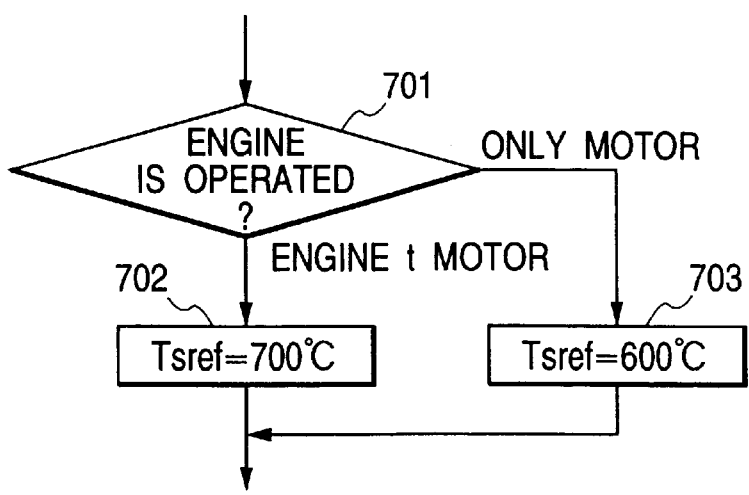
FIG. 21 is a flowchart of a subprogram to determine a target value of a controlled temperature of a heater installed in a gas concentration sensor according to the sixth embodiment.

FIG. 21 shows a subprogram for feedback-controlled power supply to the heater 35 of the A/F sensor 30 performed in the sixth embodiment which is a modification of the one shown in FIGS. 7 or 14. Specifically, steps 701, 702, and 703 are executed instead of steps 203, 204, and 205 in FIG. 7 or steps 303, 304, 305, and 306 in FIG. 14.

In step 701, an operating condition of the vehicle is monitored to determine whether the internal combustion engine and the electric generator-motor are both operating or only the electric generator-motor is operating. If both are operating, then the routine proceeds to step 702 wherein the target temperature value Tsref is set to 700° C. Alternatively, if only the electric generator-motor is operating meaning that the internal combustion engine is stopped and that an output of the A/F sensor 30 needs not be used in the feedback control of the air-fuel ratio, then the routine proceeds to step 703 wherein the target temperature value Tsref is set to 600° C. This realizes the power saving in the hybrid vehicle, thus resulting in a decrease in fuel consumption.

Additionally, during idle modes of engine operation in which the feedback control of the air-fuel ratio is stopped, the target temperature value Tsref may also be decreased or the power supply to the heater 35 may alternatively be stopped.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

For example, the above embodiments each regulate an electric power supply to the heater under feedback control based on the sensor element temperature Ts, but may alternatively regulate it based on an internal resistance of the gas concentration sensor. Specifically, when the feedback control of the air-fuel ratio of mixture supplied to the engine 10 is being performed, a controlled target value of the internal resistance of the gas concentration sensor is set to a lower value which enables the gas concentration sensor to provide an accurate output, while when the feedback control is not performed, the controlled target value is set to a higher value to decrease the power supply to the heater. Alternatively, when the air-fuel ratio of mixture supplied to the engine 10 is being controlled on either of the rich and lean sides, the controlled target value of the internal resistance may be set to a lower value, while when the air-fuel ratio of mixture is being controlled to be brought into agreement with the stoichiometric air-fuel ratio, the controlled target value may be set to a higher value.

The feedback control of a power supply to the heater may be performed based on the temperature or resistance of the heater. Usually, the resistance of a heater increases as the temperature thereof is elevated.

For example, when the feedback control of the air-fuel ratio of mixture supplied to the engine 10 is being performed, a controlled target value of the temperature or resistance of the heater is set to a higher value which enables the gas concentration sensor to provide an accurate output, while when the feedback control is not performed, the controlled target value is set to a lower value to decrease the power supply to the heater. Alternatively, when the air-fuel ratio of mixture is being controlled on either of the rich and lean sides, the controlled target value of the temperature or resistance of the heater may be set to a higher value, while when the air-fuel ratio of mixture is being controlled to be brought into agreement with the stoichiometric air-fuel ratio, the controlled target value may be set to a lower value.

The feedback control of a power supply to the heater may be performed so as to bring the power supply into agreement with a target value. For example, when the feedback control of the air-fuel ratio of mixture supplied to the engine 10 is being performed, the target value of the power supply to the heater is set to a higher value which enables the gas concentration sensor to provide an accurate output, while when the feedback control is not performed, the target value is set to a lower value to decrease the power supply to the heater. Alternatively, when the air-fuel ratio of mixture is being controlled on either of the rich and lean sides, the target value may be set to a higher value, while when the air-fuel ratio of mixture is being controlled to be brought into agreement with the stoichiometric air-fuel ratio, the target value may be set to a lower value.

The duty factor-controlled signal DUTY outputted from the heater control circuit 25 to control the temperature of the heater may be regulated based on whether the feedback control of the air-fuel ratio of mixture supplied to the engine 10 is being performed or not or whether the air-fuel ratio of mixture is controlled to be brought into agreement with the stoichiometric air-fuel ratio or not.

The sensor element temperature Ts is determined as a function of the sensor element impedance Zac and used in the feedback control of a power supply to the heater, but a dc resistance value Ri of the sensor element may alternatively be used in the feedback control of the power supply to the heater.

Figure 22:
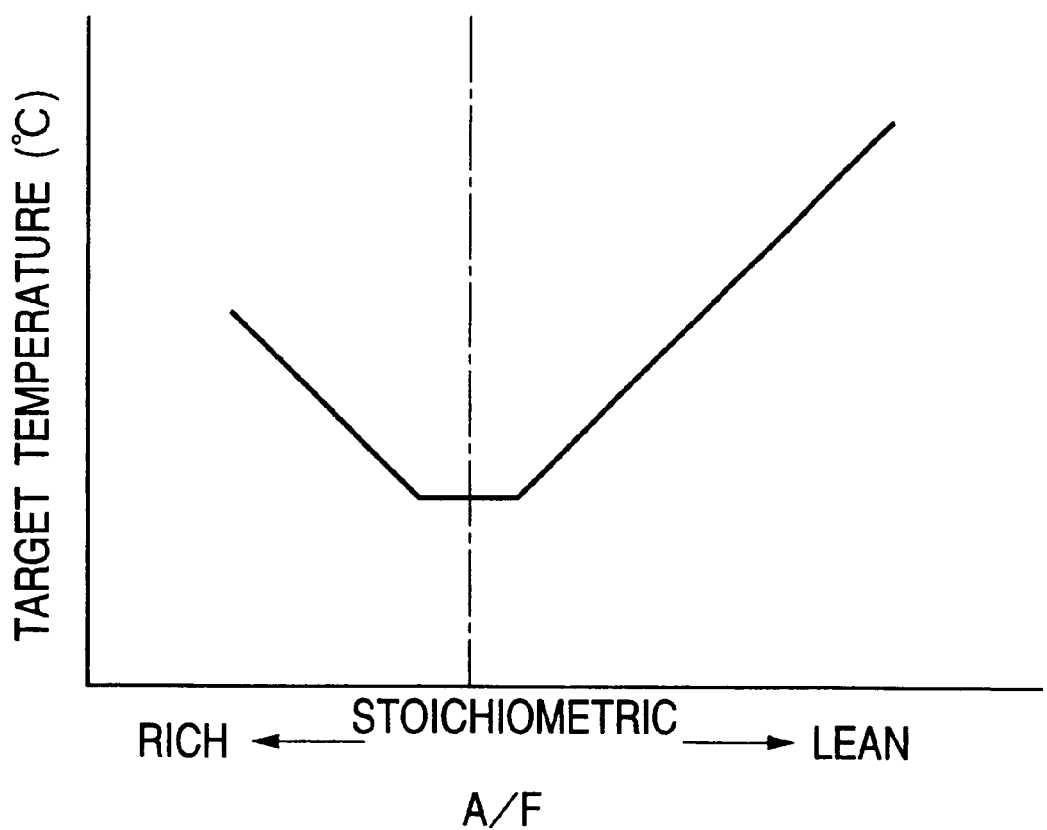
FIG. 22 is a map which shows a relation between a target temperature value of a sensor element or a heater of a gas concentration sensor and an air-fuel ratio.

The target temperature value Tsref or a controlled target value of the temperature of the heater may be determined by look-up using a map, as shown in FIG. 22. Specifically, if an output of the gas concentration sensor indicates the stoichiometric air-fuel ratio, the target value is set to the lowest temperature. If the output of the gas concentration sensor indicates a lean or rich mixture, the target value is set to a higher temperature as the mixture is shifted away from the stoichiometric air-fuel ratio.

The target temperature value Tsref or the controlled target value of the temperature of the heater may also be changed based on whether an output of the gas concentration sensor is required in the feedback control of the air-fuel ratio of mixture during warm-up modes of engine operation or not. For example, if the output of the gas concentration sensor is required, the target value is set to a higher temperature to elevate the temperature of the heater quickly. Alternatively, if the output of the gas concentration sensor is not required, the target value is set to a lower temperature to elevate the temperature of the heater slowly.

In step 206 in FIG. 7, the deterioration correction coefficient Ks is determined as a function of the degree of deterioration of the A/F sensor 30 by look-up using the map in FIG. 10 for correcting the target temperature value Tsref, but may alternatively be determined using a relation between the internal resistance of the sensor element and the power supply to the heater 35 under the condition that a condition wherein the temperature of exhaust gasses of the engine 10 is stable. For example, if the A/F sensor is deteriorated so that the internal resistance thereof is increased, the deterioration correction coefficient Ks is determined so as to increase the duty factor of the duty factor-controlled signal DUTY.

The solid electrolyte body 31 and the diffused resistance layer 32 may be formed with a laminated plate element. For example, U.S. Pat. No. 5,573,650, issued Nov. 12, 1996 to Fukaya et al., teaches such a structure, disclosure of which is incorporated herein by reference.

The feedback control of the air-fuel ratio of mixture supplied to the engine 10 may be performed using an output of an NOx sensor such as the one shown in FIGS. 18 or 20. Specifically, an instant air-fuel ratio of mixture is monitored using an output signal of the NOx sensor to bring the air-fuel ratio into agreement with a target value. In this case, the target temperature value Tsref or a controlled target value of the temperature of the heater may be changed in the same manner as described above based on whether the output of the NOx sensor is required in the feedback control of the air-fuel ratio of mixture or not.

Figure 23:
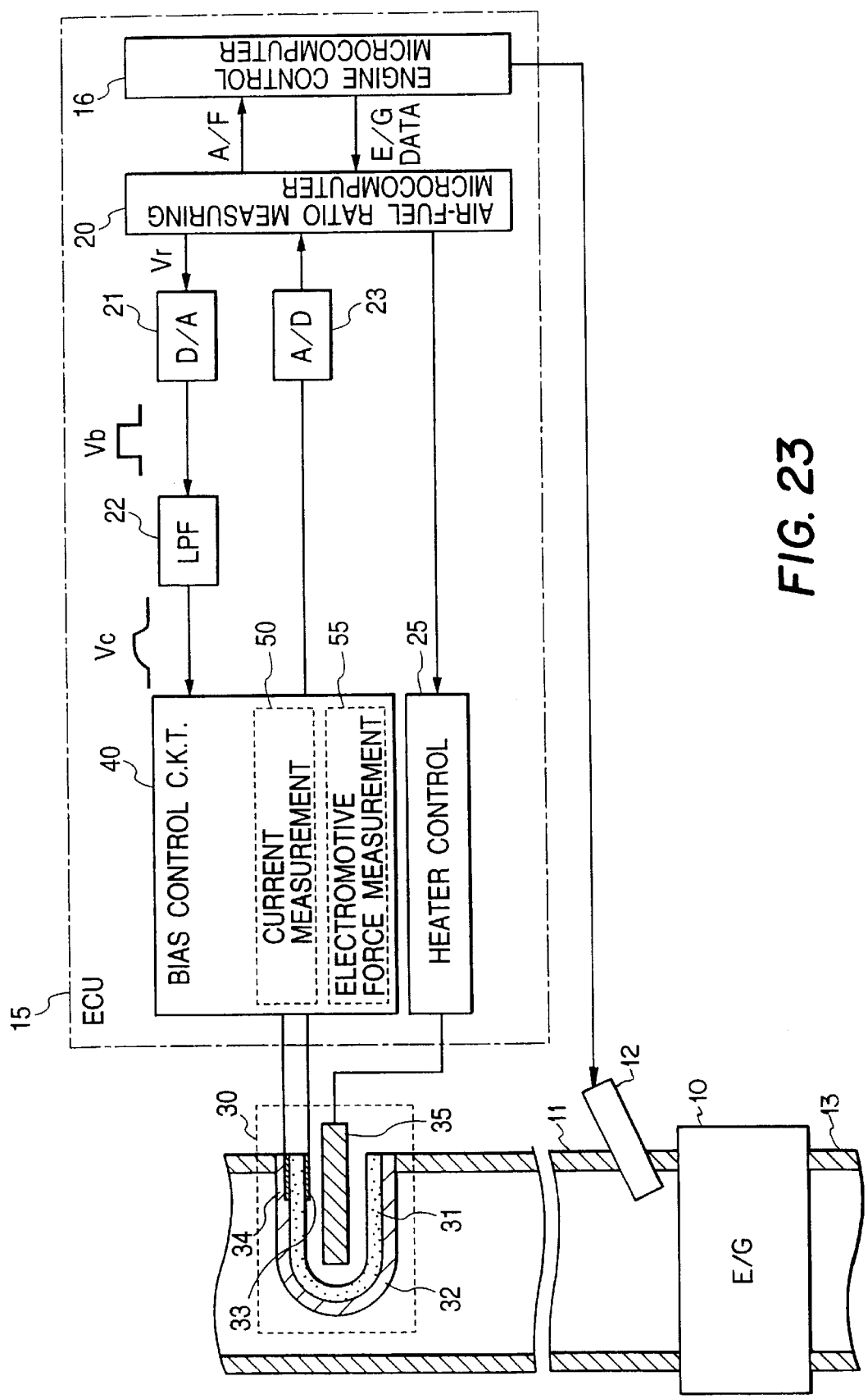
FIG. 23 is a block diagram which shows an alternate arrangement of a gas sensor control system according to the invention.2

The air-fuel ratio control system, as described above, has the A/F sensor 30 installed in the exhaust pipe 13 of the engine 10 to measures an oxygen content in exhaust gasses, but, as illustrated in FIG. 23, may install a similar A/F sensor in an induction pipe of the engine 10 instead of or in addition to the A/F sensor 30 to measure an oxygen content in induction gasses for use in controlling the air-fuel ratio of mixture. In this case, an output of the A/F sensor installed in the induction pipe may be used to control an exhaust gas recirculation (EGR) system. The air-fuel ratio control system may reflect a controlled condition of the EGR system on control of the air-fuel ratio of mixture and change the target temperature value Tsref or a controlled target value of the temperature of the heater based on whether the output of the A/F sensor is required to control the EGR or not. If not, the target temperature value Tsref or the controlled target value of the temperature of the heater is set to a lower temperature. Particularly, hybrid vehicles need not control the EGR when an internal combustion engine is stopped and thus may decrease the target temperature value Tsref or the controlled target value of the temperature of the heater or alternatively cut the power supply to the heater.

The output of the A/F sensor installed in the induction pipe of the engine may also be employed in an evaporative emission control system. Specifically, the concentration of fuel vapors which are evaporated within a fuel tank, accumulated in a canister, and then discharged into the induction pipe of the engine is measured by the A/F sensor to correct the quantity of fuel injected into the engine. In this case, the air-fuel ratio control system may change the target temperature value Tsref or the controlled target value of the temperature of the heater based on whether the fuel vapors are being purged from the canister or not. If it is not required to purge the fuel vapors from the canister, the air-fuel ratio control system sets the target temperature value Tsref or the controlled target value of the temperature of the heater a lower temperature or cut the power supply to the heater.

The present invention is used with the air-fuel ratio control system equipped with the A/F sensor 30 designed to measure an oxygen content in exhaust gasses or the gas concentration sensor 100 or 200 designed to measure a nitrogen oxide (NOx) content in exhaust gasses, but may alternatively be used with air-fuel ratio control systems equipped with another type of gas sensor which measures hydro carbon (HC) or carbon monoxide (CO).

What is claimed is:

1. A heater control apparatus for controlling power supplied to a heater used to heat a solid electrolyte-made sensing element of a gas concentration sensor up to a temperature at which the sensing element is activated to provide a desired gas concentration output, said desired gas concentration output intermittently being read by automotive control circuitry, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein said target temperature value-determining circuit decreases the target temperature value during periods of time in which the gas concentration output from the gas concentration sensor is not required to be read by the automotive control circuitry and wherein said target value-determining circuit increases the target temperature value during periods of time in which the gas concentration output is required to be read by the automotive control circuitry.

2. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein the gas concentration sensor measures the concentration of a given gaseous component contained in either of exhaust gasses and induction gasses of an internal combustion engine of a vehicle and provides the gas concentration output indicative thereof for use in feedback control of an air-fuel ratio of mixture supplied to the internal combustion engine, said heater control apparatus further comprising a decision circuit deciding whether or not a given control execution condition is met which is used in determining whether or not the feedback control of the air-fuel ratio is to be executed, and wherein said target temperature value-determining circuit changes the target temperature value depending upon a decision of said decision circuit.

3. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein the gas concentration sensor measures the concentration of a given gaseous component contained in either of exhaust gasses and induction gasses of an internal combustion engine of a vehicle to determine an air-fuel ratio for use in feedback control of an air-fuel ratio of mixture supplied to the internal combustion engine, and wherein said target temperature value-determining circuit changes the target temperature value as a function of the air-fuel ratio determined by the gas concentration sensor.

4. A heater control apparatus as set forth in claim 3, wherein when the air-fuel ratio determined by the gas concentration sensor is leaner than a stoichiometric air-fuel ratio, said target temperature value-determining circuit elevates the target temperature value above that determined when the air-fuel ratio determined by the gas concentration sensor shows the stoichiometric air-fuel ratio.

5. A heater control apparatus as set forth in claim 3, wherein when the air-fuel ratio determined by the gas concentration sensor is richer than a stoichiometric air-fuel ratio, said target temperature value-determining circuit elevates the target temperature value above that determined when the air-fuel ratio determined by the gas concentration sensor shows the stoichiometric air-fuel ratio.

6. A heater control apparatus as set forth in claim 3, wherein when a mixture supplied to the internal combustion engine is controlled to be leaner than a stoichiometric air-fuel ratio, said target temperature value-determining circuit elevates the target temperature value above that when the mixture supplied to the internal combustion engine is controlled to have the stoichiometric air-fuel ratio.

7. A heater control apparatus as set forth in claim 3, wherein when a mixture supplied to the internal combustion engine is controlled to be richer than a stoichiometric air-fuel ratio, said target temperature value-determining circuit elevates the target temperature value above that when the mixture supplied to the internal combustion engine is controlled to have the stoichiometric air-fuel ratio.

8. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein the gas concentration sensor is designed to measure the concentration of oxygen contained in either of exhaust gasses and induction gasses of an internal combustion engine of a vehicle for use in an air-fuel ratio feedback control system for controlling an air-fuel ratio of mixture supplied to the internal combustion engine, the gas concentration sensor being controlled by the air-fuel ratio feedback control system to selectively output an electromotive force signal according the concentration of oxygen when the air-fuel ratio of mixture lies within a narrower range across a stoichiometric air-fuel ratio and a limiting current signal changing linearly with a change in the air-fuel ratio of mixture when the air-fuel ratio changes within a wider range from a rich air-fuel ratio to a lean air-fuel ratio, and wherein said target temperature value-determining circuit changes the target temperature value depending upon whether the gas concentration sensor is outputting the electromotive force signal or the limiting current signal.

9. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein the gas concentration sensor is designed to measure the concentration of oxygen contained in either of exhaust gasses and induction gasses of an internal combustion engine of a vehicle for use in an air-fuel ratio feedback control system for controlling an air-fuel ratio of mixture supplied to the internal combustion engine, the gas concentration sensor being controlled by the air-fuel ratio feedback control system to selectively output an electromotive force signal according the concentration of oxygen when the air-fuel ratio of mixture lies within a narrower range across a stoichiometric air-fuel ratio and a limiting current signal changing linearly with a change in the air-fuel ratio of mixture when the air-fuel ratio changes within a wider range from a rich air-fuel ratio to a lean air-fuel ratio, and wherein said target temperature value-determining circuit changes the target temperature value depending upon whether the gas concentration sensor is controlled by the air-fuel ratio feedback control system to output the electromotive force signal or the limiting current signal.

10. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein the gas concentration sensor is a complex gas sensor designed to measure concentrations of a plurality of gaseous components and to output a plurality of signals indicating the respective concentrations of the plurality of gaseous components;

said heater control apparatus further comprising an output decision circuit that decides which of said plurality of signals is to be outputted from said gas concentration sensor, and said target temperature value-determining circuit changing the target temperature value based on a decision of said output determination circuit as to which of said plurality of signals is to be outputted from said gas concentration sensor.

11. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the sensing element of the gas concentration sensor into agreement with a target temperature value; and a target temperature value-determining circuit determining the target temperature value as a function of an environmental condition in which the gas concentration sensor is used and a use of the gas concentration sensor;

wherein the gas concentration sensor measures the concentration of a given gaseous component contained in either of exhaust gasses and induction gasses of an internal combustion engine mounted in a hybrid vehicle which uses both the internal combustion engine and an electric motor as a power source for driving the hybrid vehicle, and wherein said target temperature value-determining circuit decreases the target temperature value when the internal combustion engine is at rest.

12. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring one of a temperature of the sensing element of the gas concentration sensor and a temperature of the heater into agreement with a target temperature value; and a target temperature value-determining circuit determining the target temperature value as a function of an environmental condition in which the gas concentration sensor is used and a use of the gas concentration sensor;

said heater control apparatus further comprising a sensor deterioration determining circuit determining the degree of deterioration of the gas concentration sensor, and wherein said target temperature value-determining circuit corrects the target temperature value so as to compensate for the degree of deterioration of the gas concentration sensor determined by said sensor deterioration determining circuit.

13. A heater control apparatus for controlling power supplied to a heater used to heat a solid electrolyte-made sensing element of a gas concentration sensor up to a temperature at which the sensing element is activated to provide a desired gas concentration output for controlling a preselected variable used in a given feedback control system, said heater control apparatus comprising:

a power supply-controlling circuit controlling an electric power supply to the heater to bring one of a temperature of the sensing element of the gas concentration sensor and a temperature of the heater into agreement with a target temperature value; and a target temperature value-determining circuit determining the target temperature value as a function of the preselected variable used in the feedback control system.

14. A heater control apparatus for controlling power supplied to a heater used to heat a solid electrolyte-made sensing element of a gas concentration sensor up to a temperature at which the sensing element is activated to provide a desired gas concentration output, said desired gas concentration output intermittently being read by automotive control circuitry, said heater control apparatus comprising:

a power supply-controlling circuit controlling an electric power supply to the heater to bring a temperature of the heater into agreement with a target temperature value; and a target temperature value-determining circuit determining the target temperature value as a function of an environmental condition in which the gas concentration sensor is used and a use of the gas concentration sensor;

wherein said target temperature value-determining circuit decreases the target temperature value during periods of time in which the gas concentration output from the gas concentration sensor is not required to be read by the automotive control circuitry and wherein said target value-determining circuit increases the target temperature value during periods of time in which the gas concentration output is required to be read by the automotive control circuitry.

15. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the heater into agreement with a target temperature value; and a target temperature value-determining circuit determining the target temperature value as a function of an environmental condition in which the gas concentration sensor is used and a use of the gas concentration sensor;

wherein the gas concentration sensor measures the concentration of a given gaseous component contained in either of exhaust gasses and induction gasses of an internal combustion engine of a vehicle and provides the gas concentration output indicative thereof for use in feedback control of an air-fuel ratio of mixture supplied to the internal combustion engine, said heater control apparatus further comprising a decision circuit deciding whether or not a given control execution condition is met which is used in determining whether or not the feedback control of the air-fuel ratio is to be executed, and wherein said target temperature value-determining circuit changes the target temperature value depending upon a decision of said decision circuit.

16. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:

a power supply-controlling circuit controlling an electric power supply to the heater to bring a temperature of the heater into agreement with a target temperature value; and a target temperature value-determining circuit determining the target temperature value as a function of an environmental condition in which the gas concentration sensor is used and a use of the gas concentration sensor;

wherein the gas concentration sensor measures the concentration of a given gaseous component contained in either of exhaust gasses and induction gasses of an internal combustion engine of a vehicle to determine an air-fuel ratio for use in feedback control of an air-fuel ratio of mixture supplied to the internal combustion engine, and wherein said target temperature value-determining circuit changes the target temperature value as a function of the air-fuel ratio determined by the gas concentration sensor.

17. A heater control apparatus as set forth in claim 16, wherein when the air-fuel ratio determined by the gas concentration sensor is leaner than a stoichiometric air-fuel ratio, said target temperature value-determining circuit elevates the target temperature value above that determined when the air-fuel ratio determined by the gas concentration sensor shows the stoichiometric air-fuel ratio.

18. A heater control apparatus as set forth in claim 16, wherein when the air-fuel ratio determined by the gas concentration sensor is richer than a stoichiometric air-fuel ratio, said target temperature value-determining circuit elevates the target temperature value above that determined when the air-fuel ratio determined by the gas concentration sensor shows the stoichiometric air-fuel ratio.

19. A heater control apparatus as set forth in claim 16, wherein when a mixture supplied to the internal combustion engine is controlled to be leaner than a stoichiometric air-fuel ratio, said target temperature value-determining circuit elevates the target temperature value above that when the mixture supplied to the internal combustion engine is controlled to have the stoichiometric air-fuel ratio.

20. A heater control apparatus as set forth in claim 16, wherein when a mixture supplied to the internal combustion engine is controlled to be richer than a stoichiometric air-fuel ratio, said target temperature value-determining circuit elevates the target temperature value above that when the mixture supplied to the internal combustion engine is controlled to have the stoichiometric air-fuel ratio.

21. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:
   a power supply-controlling circuit controlling an electric power supply to the heater to bring a temperature of the heater into agreement with a target temperature value; and
   a target temperature value-determining circuit determining the target temperature value as a function of an environmental condition in which the gas concentration sensor is used and a use of the gas concentration sensor;
   wherein the gas concentration sensor is designed to measure the concentration of oxygen contained in either of exhaust gasses and induction gasses of an internal combustion engine of a vehicle for use in an air-fuel ratio feedback control system for controlling an air-fuel ratio of mixture supplied to the internal combustion engine, the gas concentration sensor being controlled by the air-fuel ratio feedback control system to selectively output an electromotive force signal according the concentration of oxygen when the air-fuel ratio of mixture lies within a narrower range across a stoichiometric air-fuel ratio and a limiting current signal changing linearly with a change in the air-fuel ratio of mixture when the air-fuel ratio changes within a wider range from a rich air-fuel ratio to a lean air-fuel ratio, and wherein said target temperature value-determining circuit changes the target temperature value depending upon whether the gas concentration sensor is outputting the electromotive force signal or the limiting current signal.

22. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:
   a power supply-controlling circuit controlling an electric power supply to the heater to bring a temperature of the heater into agreement with a target temperature value; and
   a target temperature value-determining circuit determining the target temperature value as a function of an environmental condition in which the gas concentration sensor is used and a use of the gas concentration sensor;
   wherein the gas concentration sensor is designed to measure the concentration of oxygen contained in either of exhaust gasses and induction gasses of an internal combustion engine of a vehicle for use in an air-fuel ratio feedback control system for controlling an air-fuel ratio of mixture supplied to the internal combustion engine, the gas concentration sensor being controlled by the air-fuel ratio feedback control system to selectively output an electromotive force signal according the concentration of oxygen when the air-fuel ratio of mixture lies within a narrower range across a stoichiometric air-fuel ratio and a limiting current signal changing linearly with a change in the air-fuel ratio of mixture when the air-fuel ratio changes within a wider range from a rich air-fuel ratio to a lean air-fuel ratio, and wherein said target temperature value-determining circuit changes the target temperature value depending upon whether the gas concentration sensor is controlled by the air-fuel ratio feedback control system to output the electromotive force signal or the limiting current signal.

23. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:
   a power supply-controlling circuit controlling an electric power supply to the heater to bring a temperature of the heater into agreement with a target temperature value; and
   a target temperature value-determining circuit determining the target temperature value as a function of an environmental condition in which the gas concentration sensor is used and a use of the gas concentration sensor;
   wherein the gas concentration sensor is a complex gas sensor designed to measure concentrations of a plurality of gaseous components and to output a plurality of signals indicating the respective concentrations of the plurality of gaseous components;
   said heater control apparatus further comprising an output decision circuit that decides which of said plurality of signals is to be outputted from said gas concentration sensor, and
   said target temperature value-determining circuit changing the target temperature value based on a decision of said output determination circuit as to which of said plurality of signals is to be outputted from said gas concentration sensor.

24. A heater control apparatus for controlling power supplied to a heater used to heat a solid electrolyte-made sensing element of a gas concentration sensor up to a temperature at which the sensing element is activated to provide a desired gas concentration output, said heater control apparatus comprising:
   a power supply-controlling circuit controlling an electric power supply to the heater to bring a temperature of the heater into agreement with a target temperature value; and
   a target temperature value-determining circuit determining the target temperature value as a function of an environmental condition in which the gas concentration sensor is used and a use of the gas concentration sensor;
   wherein the gas concentration sensor measures the concentration of a given gaseous component contained in either of exhaust gasses and induction gasses of an internal combustion engine mounted in a hybrid vehicle which uses both the internal combustion engine and an electric motor as a power source for driving the hybrid vehicle, and wherein said target temperature value-determining circuit decreases the target temperature value when the internal combustion engine is at rest.

* * * * *